United States Patent
Garza et al.

(10) Patent No.: US 10,105,305 B2
(45) Date of Patent: Oct. 23, 2018

(54) COMPOSITIONS AND METHODS FOR PROMOTING SKIN REGENERATION AND HAIR GROWTH

(71) Applicant: THE JOHNS HOPKINS UNIVERSITY, Baltimore, MD (US)

(72) Inventors: Luis Andres Garza, Baltimore, MD (US); Amanda Marie Nelson, Hummelstown, PA (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/120,189

(22) PCT Filed: Feb. 19, 2015

(86) PCT No.: PCT/US2015/016490
§ 371 (c)(1),
(2) Date: Aug. 19, 2016

(87) PCT Pub. No.: WO2015/127002
PCT Pub. Date: Aug. 27, 2015

(65) Prior Publication Data
US 2017/0056310 A1   Mar. 2, 2017

Related U.S. Application Data

(60) Provisional application No. 62/060,598, filed on Oct. 7, 2014, provisional application No. 61/947,714, filed on Mar. 4, 2014, provisional application No. 61/941,890, filed on Feb. 19, 2014.

(51) Int. Cl.
| | |
|---|---|
| A61K 8/60 | (2006.01) |
| A61K 31/713 | (2006.01) |
| C12N 15/117 | (2010.01) |
| A61K 8/64 | (2006.01) |
| A61Q 7/00 | (2006.01) |
| C12N 15/113 | (2010.01) |

(52) U.S. Cl.
CPC ............... *A61K 8/606* (2013.01); *A61K 8/64* (2013.01); *A61K 31/713* (2013.01); *A61Q 7/00* (2013.01); *C12N 15/117* (2013.01); *C12N 15/1138* (2013.01); *C12N 2310/17* (2013.01); *C12N 2320/31* (2013.01)

(58) Field of Classification Search
CPC ...................................... A61K 8/606
See application file for complete search history.

(56) References Cited

U.S. PATENT DOCUMENTS

| | | | | |
|---|---|---|---|---|
| 2006/0211752 A1* | 9/2006 | Kohn | ................ | A61K 31/4164 514/389 |
| 2007/0031356 A1* | 2/2007 | Buchwald Hunziker | .................. | A61K 8/31 424/59 |
| 2009/0253622 A1* | 10/2009 | Van Noort | ......... | A61K 38/1709 514/1.1 |
| 2009/0285779 A1* | 11/2009 | Lebecque | ............ | A61K 31/713 424/85.4 |
| 2010/0004304 A1* | 1/2010 | Kohn | ................. | A61K 31/4164 514/396 |
| 2010/0319074 A1 | 12/2010 | Lu et al. | | |
| 2011/0082218 A1* | 4/2011 | Wertz | ....................... | A61K 8/31 514/763 |
| 2012/0115923 A1 | 5/2012 | He et al. | | |
| 2012/0238610 A1* | 9/2012 | Kohn | ................. | A61K 31/4164 514/392 |
| 2012/0308581 A1* | 12/2012 | Chemin | ............. | C07K 16/2896 424/172.1 |
| 2013/0266588 A1* | 10/2013 | Ji | ....................... | A61K 31/4706 424/172.1 |
| 2015/0202258 A1* | 7/2015 | Berger | ............... | A61K 38/1709 424/93.2 |
| 2015/0274785 A1* | 10/2015 | Li | ........................ | C07K 1/1077 514/18.7 |
| 2015/0297572 A1* | 10/2015 | Niazi | ..................... | A61K 31/16 514/375 |
| 2015/0374598 A1* | 12/2015 | Wertz | ...................... | A61K 8/31 514/763 |
| 2016/0220536 A1* | 8/2016 | Kohn | ................. | A61K 31/4164 |
| 2016/0256461 A1* | 9/2016 | Christiano | ........... | A61K 31/519 |

FOREIGN PATENT DOCUMENTS

| | | |
|---|---|---|
| CN | 101780279 A | 7/2010 |
| WO | 2007079224 A2 | 7/2007 |
| WO | 2008-109083 A2 | 9/2008 |

OTHER PUBLICATIONS

Kumar, A., et al., "Toll-like receptor 3 agonist poly(I:C)-induced antiviral response in human corneal epithelial cells" Immunology (2006) vol. 117, No. 1, pp. 11-21.

(Continued)

*Primary Examiner* — Amber D Steele
(74) *Attorney, Agent, or Firm* — Johns Hopkins Technology Ventures

(57) ABSTRACT

The present invention relates to the field of wound healing. Specifically, the present invention provides compositions and methods for promoting skin regeneration, more specifically, the generation of de novo hair follicles. In one embodiment, a method for stimulating hair follicle neogenesis in a subject comprises the step of administering to the subject an effective amount of a TLR3 agonist. In certain embodiments, the TLR3 agonist is a double stranded RNA (dsRNA). The present invention is also directed to treating common male pattern hair loss.

16 Claims, 35 Drawing Sheets
Specification includes a Sequence Listing.

(56) References Cited

OTHER PUBLICATIONS

Pan, L., et al., "Toll-like receptor 3 agonist poly I:C protects against simulated cerebral ischemia in vitro and in vivo" Acta Pharmacologica Sinica (2012) vol. 33, No. 10, pp. 1246-1253.
Schmidt, K., et al., "APC-independent activation of NK cells by the toll-like receptor 3 agonist double-stranded RNA" The Journal of Immunology (2004) vol. 172, No. 1, pp. 138-143.
Zhang, J., et al., "Toll-like receptor 3 agonist induces impairment of uterine vascular remodeling and fetal losses in CBC x DBA/2 mice" Journal of Reproductive Immunology (2007) vol. 74, No. 1, pp. 61-67.
Anderson K. V., et al. (1985). Establishment of dorsal-ventral polarity in the Drosophila embryo: the induction of polarity by the Toll gene product. Cell 42, 791-798.
Barker N. (2008). The canonical Wnt/betacatenin signalling pathway. Methods Mol Biol 468, 5-15.
Bernard J. J., et al. (2012). Ultraviolet radiation damages self non-coding RNA and is detected by TLR3. Nat Med.
Breedis C. (1954). Regeneration of hair follicles and sebaceous glands from the epithelium of scars in the rabbit. Cancer Res 14, 575-579.
Brockes J. P., et al. (2001). Regeneration as an evolutionary variable. Journal of anatomy 199, 3-11.
Carpenter A. E., et al. (2006). CellProfiler: image analysis software for identifying and quantifying cell phenotypes. Genome biology 7, RIOO.
Fan C., et al. (2011). Characterization and quantification of wound-induced hair follicle neogenesis using in vivo confocal scanning laser microscopy. Skin Res Technol 17, 387-397.
Fuchs E.,et al. (2002). Getting under the skin of epidermal morphogenesis. Nat Rev Genet 3, 199-209.
Galun E., et al. (2013). The regenerative activity of interleukin-6. Methods Mol Biol 982, 59-77.
Gay, D., et al. (2013). Fgf9 from dermal gammadelta T cells induces hair follicle neogenesis after wounding. Nat Med 19, 916-923.
Heinrich, P. C., et al. (2003). Principles of interleukin (IL)-6-type cytokine signalling and its regulation. Biochem J 374, 1-20.
Imokawa Y., et al. (2003). Selective activation of thrombin is a critical determinant for vertebrate lens regeneration. Current biology: C B 13, 877-881.
Irizarry R. A., et al. (2003). Summaries of Affymetrix GeneChip probe level data. Nucleic Acids Res 31, e15.
Ito M., et al. (2007). Wntdependent de nova hair follicle regeneration in adult mouse skin after wounding. Nature 447, 316-320.
Yamashita, M., et al. A TRIF-Independent Branch of TLR3 Signaling. Journal of Immunology, 188: (2012).
Kariko K., et al. (2004). mRNA is an endogenous ligand for Toll-like receptor 3. J Biol Chem 279, 12542-12550.
Karim, R., et al. (2011). Human papillomavirus deregulates the response of a cellular network comprising of chemotactic and proinflammatory genes. PLoS One 6, el 7848.
Kligman A. M., and Strauss J. S. (1956). The formation of vellus hair follicles from human adult epidermis. J Invest Dermatol 27, 19-23.
Koster, M. I., et al. (2004). p63 is the molecular switch for initiation of an epithelial stratification program. Genes Dev 18, 126-131.
Koster< M. I., and Roop, D.R. (2004). The role of p63 in development and differentiation of the epidermis. Journal of dermatological science 34, 3-9.
Lai, Y., et al. (2009). Commensal bacteria regulate Toll-like receptor 3-dependent inflammation after skin injury. Nat Med 15, 1377-1382.
Lamouille S., et al. (2014). Molecular mechanisms of epithelial-mesenchymal transition. Nature reviews Molecular cell biology 15, 178-196.
Lebre M. C., et al. (2007). Human keratinocytes express functional Toll-like receptor 3, 4, 5, and 9. J Invest Dermatol 127, 331-341.
Lee J., et al. (2012). Activation of innate immunity is required for efficient nuclear reprogramming. Cell 151, 547-558.
Lin Q., et al. (2012). Toll-like receptor 3 ligand polyinosinic:polycytidylic acid promotes wound healing in human and murine skin. J Invest Dermatol 132, 2085-2092.
Liu Y., et al. (2003). Keratin 15 Promoter Targets Putative Epithelial Stem Cells in the Hair Follicle Bulge. 121, 963-968.
Luis N.M.. et al. (2012a). Polycomb in Stem Cells:PRCI Branches Out. Cell Stem Cell 11, 16-21.
Luis N. M., et al. (2012b). Regulation of human epidermal stem cell proliferation and senescence requires polycomb-dependent and -independent functions of Cbx4. Cell Stem Cell 9, 233-246.
Lundberg A. M., et al. (2007). Key differences in TLR3/poly I:C signaling and cytokine induction by human primary cells: a phenomenon absent from murine cell systems. Blood 110, 3245-3252.
Melkamu T., et al. (2013). TLR3 activation evokes IL-6 secretion, autocrine regulation of Stat3 signaling and TLR2 expression in human bronchial epithelial cells. J Cell Commun Signal 7, 109-118.
Mescher A. L. (1996). The cellular basis of limb regeneration in urodeles. The International journal of developmental biology 40, 785-795.
Millar S. E. (2002). Molecular mechanisms regulating hair follicle development. J Invest Dermatol 118, 216-225.
Myung P. S., et al. (2013). Epithelial Wnt ligand secretion is required for adult hair follicle growth and regeneration. The Journal of investigative dermatology 133, 31-41.
Nelson A. M., et al. (2013). Prostaglandin D(2) Inhibits Wound-Induced Hair Follicle Neogenesis through the Receptor, Gpr44. The Journal of investigative dermatology 133, 881-889.
Sanchez Alvarado A. (2006). Planarian regeneration: its end is its beginning Cell 124, 241-245.
St-Jaques B., et al. (1998). Sonic hedgehog signaling is essential for hair development. Current biology: CB 8, 1058-1068.
Torok M. A., et al. (1999). Sonic hedgehog (shh) expression in developing and regenerating axolotl limbs. The Journal of experimental zoology 284, 197-206.
Uematsu S., and Akira S. (2007). Toll-like receptors and Type I interferons. J Biol Chem 282, 15319-15323.
Yan C., Grimm et al. (2010). Epithelial to mesenchymal transition in human skin wound healing is induced by tumor necrosis factor-alpha through bonemorphogenic protein-2. The American journal of pathology 176, 2247-2258.
Bhartiya et al., Enhanced Wound Helaing in Animal Models by Interferon and an Interferon Inducer. J Cell Physiol. 1992; 150 (2): 312-9.
Sato T., et al. Accelerated wound healing mediated by activation of Toll-like receptor 9. Wound Rep Reg 18; 586-593 (2010).
Lin, Q., et al. Impaired Wound Healing with Defective Expression of Chemokines and Recruitment of Myeloid Cells in TLR3-Deficient Mice. The Journal of Immunology, 186: 3710-3717 (2011).
Rhett J. M., et al. Novel therapies for scar reduction and regenerative healing of skin wounds. Trends in Biotechnology, 26(4); 173-180 (2008).
Occleston, N. L., et al. Prevention and reduction of scarring in the skin by Transforming Growth Factor beta 3 (TGFβ3): from laboratory discovery to clinical pharmaceutical. J. Biomater. Sci. Polymer Edn, 19(8); 1047-1063 (2008).
Dasu M. R., et al. Toll-Like Receptors in Wound Healing: Location, Accessibility, and Timing. Journal of Investigative Dermatology 132,1955-1958 (2012).

* cited by examiner

E

F

A

B

C

D

F

Control    Poly (I:C)

G

| Gene Symbol | Gene Name | p-value | Fold Δ | Gene Function |
|---|---|---|---|---|
| IFIT1 | Interferon-Induced Protein With Tetratricopeptide Repeats 1 | 3.12E-05 | 3.9194 | Interferon induced; anti-viral RNA binding protein |
| LCE3 | Late Cornified Envelope 3 | 1.27E-02 | 3.6914 | Precursor of cornified envelope |
| IFI44 | Interferon-Induced 44kDa protein | 1.81E-05 | 3.6779 | Interferon induced; microtubular structure |
| OAS1 | 2',5' Oligosynthetase 1 | 1.35E-04 | 2.7335 | Innate immune response to viral infection |
| ISG15 | Interferon Stimulated Gene 15 | 8.24E-05 | 2.6225 | Activated by IFNs; Ubiquitin-like protein; targets RIG-I |
| IRF7 | Interferon Regulatory Factor 7 | 2.54E-06 | 2.2975 | Innate immune response against DNA/RNA virus |
| OAS2 | 2',5' Oligosynthetase 2 | 1.73E-03 | 2.2851 | Innate immune response to viral infection |
| CXCL11 | Chemokine (C-X-C Motif) Ligand 11 | 1.36E-04 | 2.1059 | Induced by IFNs, skin immune response |
| OAS3 | 2',5' Oligosynthetase 3 | 1.69E-04 | 2.0748 | Innate immune response to viral infection |
| RSAD2 | Radical S-Adenosyl Methionine Domain Containing 2 | 1.78E-04 | 2.0589 | Interferon-inducible; anti-viral activity |
| OASL | 2',5' Oligosynthetase-Like | 4.49E-04 | 1.9994 | Innate immune response to viral infection |
| BST2 | Bone Marrow Stromal Antigen | 7.70E-05 | 1.9656 | IFN-induced anti-viral factor |
| DHX58 | DEXH (Asp-Glu-X-His) Box Polypeptide 58 | 4.28E-04 | 1.9042 | Regulates DDX58; directly binds dsRNA |
| DDX58/RIG-I | Retinoic Acid-Inducible Gene 1 Protein | 7.15E-04 | 1.8025 | Recognizes dsRNA; innate immune response |
| PARP14 | Poly (ADP-Ribose) Polymerase Family, Member 14 | 2.36E-04 | 1.7923 | Post-translational modification of histones after DNA damage |
| XAF1 | XIAP Associated Factor 1 | 3.41E-04 | 1.7059 | Negative regulator of "inhibitor of apoptosis" (XIAP) proteins |
| HERC6/HERC5 | HECT And RLD Domain Containing E3 Ubiquitin Protein Ligase | 2.20E-04 | 1.6458 | Ubiquitin ligase |
| IFI35 | Interferon-Induced 35kDa protein | 3.86E-05 | 1.6281 | Interferon induced |
| CXCL9 | Chemokine (C-X-C Motif) Ligand 9 | 7.13E-02 | 1.6075 | T-cell trafficking, immune and inflammatory response |
| MMP9 | Matrix Metalloproteinase 9 (Gelatinase) | 4.07E-02 | 1.6037 | Tissue remodeling |
| CMPK2 | Cytidine Monophosphate (UMP-CMP) Kinase 2 | 4.71E-04 | 1.5895 | Nucleotide synthesis salvage pathway |
| GBP4 | Guanylate Binding Protein 4 | 2.75E-02 | 1.3757 | Induced by IFNs; hydrolyzes GTP |
| DEFB103B | Beta-Defensin 3 | 8.88E-02 | 1.2254 | Antimicrobial peptide |
| HELZ2 | Helicase With Zinc Finger | 3.28E-01 | 1.1411 | Helicase |
| TRIM5 | Tripartite Motif Containing 5 | 2.75E-04 | 1.1368 | Blocks viral replication |

| Gene Symbol | Fold Δ | P-value |
|---|---|---|
| IL-6 | 3.348 | 0.0253 |
| TNFAIP6 | 2.518 | 0.0498 |
| SOCS3 | 2.183 | 0.0317 |
| SERPINE1 | 2.175 | 0.0141 |
| Fos | 2.02 | 0.000291 |

| Gene Symbol | Fold Δ | P-value |
|---|---|---|
| Wdr92 | 6.26 | 0.0150 |
| Ccl24 | 4.23 | 0.0065 |
| Ptgs2 | 3.72 | 0.0042 |
| Il-6 | 3.35 | 0.0253 |
| Nr4a1 | 2.92 | 0.0012 |
| Cxcl2 | 2.52 | 0.0467 |
| Cxcl1 | 2.10 | 0.0025 |
| Il-1b | 1.93 | 0.0175 |
| Ccl3 | 1.79 | 0.0186 |
| Il-10 | 1.71 | 0.0341 |

↑ high WHN phenotype

Interleukins
Chemokines
Cytokines

| GO Bio Function Term | # of genes | P-value |
|---|---|---|
| Hematological Function | 195 | $0.00001 < P < 0.01$ |
| Inflammatory response | 110 | $0.00001 < P < 0.01$ |
| Infection mechanism | 105 | $0.0001 < P < 0.01$ |
| Cell-mediated immunity | 93 | $0.00001 < P < 0.01$ |
| Organism development | 77 | $0.0001 < P < 0.01$ |

SEQUENCE LISTING

```
<160> NUMBER OF SEQ ID NOS: 7

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 9
<212> TYPE: DNA
<213> ORGANISM: Artificial Sequence
<220> FEATURE:
<223> OTHER INFORMATION: Amplicon for Gli2 promoter site 4 encompasses
      TTCCAGGAA (SEQ ID NO:2) on chr2: 121621123-121621782 in the Encode
      database

<400> SEQUENCE: 2 ttccaggaa                                                              9

<210> SEQ ID NO 3
<211> LENGTH: 23
<212> TYPE: DNA
<213> ORGANISM: Artificial Sequence
<220> FEATURE:
<223> OTHER INFORMATION: Forward primer for Gli2 promoter site 4

<400> SEQUENCE: 3
cacagataag ctgagtcaca gga                                             23

<210> SEQ ID NO 4
<211> LENGTH: 19
<212> TYPE: DNA
<213> ORGANISM: Artificial Sequence
<220> FEATURE:
<223> OTHER INFORMATION: Reverse primer for Gli2 promoter site 4

<400> SEQUENCE: 4
tcctgttcac attgacgcc                                                  19

<210> SEQ ID NO 5
<211> LENGTH: 9
<212> TYPE: DNA
```

```
-continued

<213> ORGANISM: Artificial Sequence
<220> FEATURE:
<223> OTHER INFORMATION: Amplicon for Beta-catenin promoter site 4
      encompasses TTCCTGGAA (SEQ ID NO:5) on chr3: 41264037-41264357 in
      the Encode database.

<400> SEQUENCE: 5 ttcctggaa                                                                        9

<210> SEQ ID NO 6
<211> LENGTH: 22
<212> TYPE: DNA
<213> ORGANISM: Artificial Sequence
<220> FEATURE:
<223> OTHER INFORMATION: Forward primer for Beta-catenin promoter site 4

<400> SEQUENCE: 6
tgcctttgca tcaacaacaa gg                                                        22

<210> SEQ ID NO 7
<211> LENGTH: 23
<212> TYPE: DNA
<213> ORGANISM: Artificial Sequence
<220> FEATURE:
<223> OTHER INFORMATION: Reverse primer for Beta-catenin promoter site 4

<400> SEQUENCE: 7
tcagaaacca actggtcatg tct                                                       23
```

COMPOSITIONS AND METHODS FOR PROMOTING SKIN REGENERATION AND HAIR GROWTH

CROSS-REFERENCE TO RELATED APPLICATIONS

This application is a 35 U.S.C. § 371 U.S. national entry of International Application PCT/US2015/016490, having an international filing date of Feb. 19, 2015, which claims the benefit of U.S. Provisional Application No. 61/941,890, filed Feb. 19, 2014; U.S. Provisional Application 61/947,714, filed Mar. 4, 2014; U.S. Provisional Application No. 62/060,598, filed Oct. 7, 2014, the content of each of the aforementioned applications is herein incorporated by reference in their entirety.

STATEMENT OF GOVERNMENTAL INTEREST

This invention was made with government support under grant no. AR055666 and grant no. AR064297, each awarded by the National Institutes of Health. The government has certain rights in the invention.

FIELD OF THE INVENTION

The present invention relates to the field of regeneration. Specifically, the present invention provides compositions and methods for promoting skin regeneration, more specifically, the generation of de novo hair follicles.

INCORPORATION-BY-REFERENCE OF MATERIAL SUBMITTED ELECTRONICALLY

This application contains a sequence listing. It has been submitted electronically via EFS-Web as an ASCII text file entitled "P12197-04_ST25.txt." The sequence listing is 2,216 bytes in size, and was created on Feb. 17, 2015. It is hereby incorporated by reference in its entirety.

BACKGROUND OF THE INVENTION

Animals across diverse phyla can regenerate lost structures, a capacity that is considerably more limited in mammals. Several chordate species including urodele salamanders and teleost fish can regenerate appendages and solid organs, yet among mammals such adult organogenesis is rarely—if ever—observed. An important exception is wound-induced hair neogenesis (WIHN), a phenomenon in which skin and hair follicles are regenerated following large, full thickness wounds in mice or rabbits (Breedis, 1954; Ito et al., 2007) The complete regeneration observed in WIHN is in marked contrast to the fibrotic scarring that typically results from cutaneous wound healing. Regenerated hair follicles are complex mini-organs with disparate cell types, dedicated neurovascular support, and a distinct stem cell compartment located in the bulge region. These stem cells not only repopulate hair follicles throughout life, but also aid in skin re-epithelialization after wounding, pointing to the potential therapeutic relevance of WIHN (Ito et al., 2007). As WIHN represents a rare example of adult organogenesis in mammals, understanding its mechanisms could aid in efforts to regenerate other structures.

While originally described in the 1940s, WIHN has only recently been characterized in morphogenic and molecular detail (Breedis, 1954; Gay et al., 2013; Ito et al., 2007; Kligman and Strauss, 1956; Myung et al., 2013; Nelson et al., 2013). Following complete excision of skin down to fascia, wounds on the backs of mice are closed through initial contracture and then reepithelialization. Subsequently, hair follicle morphogenesis ensues with recapitulation of events that occur during embryonic hair development. Formation and invagination of epithelial placodes in the epidermis, induction of adjacent dermal papillae, and ultimately, elaboration of distinct hair cell subtypes are observed (Ito et al., 2007). Follicle-associated structures such as sebaceous glands are also regenerated. Regenerated follicles transit through multiple hair cycles, just like neighboring hairs from unwounded skin (Ito et al., 2007). Therefore, WIHN represents functional regeneration rather than mere wound repair through scarring.

Developmental pathways required for embryonic organogenesis are reactivated following trauma. In axolotl limb regeneration for example, Shh signaling is activated at the site of injury in the residual limb much as it is induced in the zone of polarizing activity during limb development (Torok et al., 1999). Similarly, during WIHN, signaling pathways utilized in embryonic hair formation reemerge after wounding. Activation of the canonical Wnt pathway is one of the earliest events observed in follicular morphogenesis. Wnt activation occurs around E15 in mice as the undifferentiated epithelium begins to condense into epithelial placodes at sites of future follicle formation (Millar, 2002). Similarly, after cutaneous wounding, the Wnt ligand, Wnt10b, and the Wnt effector, Lef1, are induced after re-epithelialization is complete, but prior to the emergence of new follicles (Ito et al., 2007). Wnt pathway activation is critical for hair morphogenesis during both development and regeneration, as mice deficient in Wnt signaling fail to generate hairs (Ito et al., 2007; Myung et al., 2013). Secondary to Wnt activation during follicular development, Shh signaling is induced in epithelial placodes and underlying dermal papillae. Activation of the Shh pathway contributes to subsequent hair follicle invagination and morphogenesis (St-Jacques et al., 1998). The Shh pathway is similarly induced during adult hair follicle regeneration. Other molecular details of hair regeneration are shared with hair development including expression of the hair cytokeratin Krt17 and activation of alkaline phosphatase activity in dermal papillae (Ito et al., 2007).

While downstream morphogenic events in WIHN parallel those in hair development, the signals triggering reactivation of these programs in adult regeneration are unclear. To initiate regeneration organisms must first sense a loss of tissue integrity. Candidate signals include molecules liberated from damaged tissues as well as mediators released by infiltrating immune cells. In newts and axolotls, activation of thrombin is a key early event in regeneration. Inhibition of thrombin activation abrogates lens regeneration in newts, for example (Imokawa and Brockes, 2003). Recently it has been shown that FGF9 released from γδ T cells several days after wounding promotes hair regeneration in rodents (Gay et al., 2013). However, the most proximal signals released by damaged keratinocytes to initiate regeneration in the skin remain unknown. Discovery of such damage-associated signals may explain why wound healing during WIHN proceeds with regeneration whereas most cutaneous wound healing in mammals leads to fibrotic scarring. Identifying these molecules may also suggest therapeutic approaches to promote skin and hair regeneration and reduce fibrosis.

To identify molecular events that initiate regeneration, we exploited the natural variation in regenerative capacity observed in various mouse strains. Through gene expression screening of healed wounds prior to regeneration, we identified the pattern recognition receptor, Toll-like Receptor 3 (TLR3), as a critical regulator of cutaneous regeneration, as it is up-regulated in highly regenerative mice. We identified dsRNA released from damaged cells as key triggers of the regeneration process through their activation of TLR3. The ensuing damage-induced signaling cascade prevents normal keratinocyte differentiation and promotes the acquisition of stem cell features in keratinocytes. Furthermore, TLR3 activation initiates molecular events in the hair morphogenic program, with activation of canonical Wnt, Shh pathways and EDAR resulting in augmented hair follicle neogenesis. Thus, TLR3 activation by dsRNA links damage sensing after wounding to the earliest molecular events in hair regeneration. These results uncover a novel role for TLR3 as a master regulator of regeneration in the skin.

SUMMARY OF THE INVENTION

The present invention is based, at least in part, on the discovery that TLR3 agonists can stimulate hair follicle neogenesis. Adult organogenesis is a goal of regenerative medicine and can be studied in mini-organs such as hair follicles. Although loss of an adult mammalian hair follicle was once considered permanent, hair follicle neogenesis, which recapitulates embryogenesis, can occur after skin wounding. This process is regulated by Wnts and FGFs but the signals that initiate neogenesis are not known. Gene microarray analysis, in mice at sites of skin wounding reveals that hair follicle neogenesis is significantly correlated to a TLR3 signaling signature. Furthermore, TLR3, its ligand dsRNA, and downstream TLR3 signals (IL-6, STAT3 and TAp63) are each activated during wounding and required to induce hair follicle regeneration through a mechanism that involves the activation of Wnt and Shh pathways and inhibition of keratinocyte differentiation. Taken together, these data link TLR3 activation to the earliest events of tissue damage and later hair follicle neogenesis, providing a new therapeutic target to promote hair follicle regeneration.

Accordingly, in one aspect, the present invention provides methods and compositions useful for stimulating hair follicle neogenesis. In one embodiment, a method for stimulating hair follicle neogenesis in a subject comprises the step of administering to the subject an effective amount of a TLR3 agonist. In certain embodiments, the TLR3 agonist is a double stranded RNA (dsRNA). In a specific embodiment, the subject has alopecia. In another embodiment, the subject is bald. In a further embodiment, the subject has a wound. The present invention also provides a method for treating a scar in a subject comprising the step of administering to the subject an effective amount of a TLR3 agonist.

In particular embodiments, the TLR3 agonist is administered directly to a site on the subject that requires hair follicle neogenesis. In a specific embodiment, the TLR3 agonist is administered topically. In another embodiment, the TLR3 agonist is administered by injection. In certain embodiments, wherein the TLR3 agonist is Polyinosinic:polycytidylic acid (Poly I:C). The TLR3 agonist can also be Hiltonol® or Ampligen®. In another embodiment, the TLR3 agonist comprises IPH3102.

The present invention also provides for the use of TLR3 agonists (e.g., dsRNA) as a direct means of stimulating hair neogenesis topically, either as a superficial injection, topical cream or similar method. The compositions of the present invention can also be used in a method to treat removed cells to enhance their ability for regeneration and hair follicle neogenesis, and then implant such cells into a subject. The compositions of the present invention can also be used to activate keratinocytes for use in drug screens to identify compounds that enhance or inhibit the ability for hair neogenesis, and specifically, wnt pathway activation.

In another aspect, the present invention can be used to alter skin identity. More specifically, evidence presented herein demonstrates that TLR3 agonists (e.g., dsRNA) can be used to de-differentiate cells. Such cells can be used in various applications including, but not limited to, induce volar skin at a stump site in amputees, alopecias, scars, discolored skin (e.g., port wine stains). The compositions and methods of the present invention can also be used in conjunction with the methods and compositions disclosed in Garza et al., PCT International Application No. PCT/US2013/038914 (PCT Publication No. WO2013/166045), which is hereby incorporated by reference in its entirety.

In yet another aspect, the present invention provides methods and compositions useful for treating common male pattern hair loss. In one embodiment, a method for treating common male pattern hair loss in a subject comprises the step of administering to the subject an effective amount of a TLR3 agonist. In certain embodiments, the TLR3 agonist is a double stranded RNA (dsRNA). In particular embodiments, the TLR3 agonist is administered directly to the site of hair loss on the subject. In specific embodiments, the TLR3 agonist is administered topically. In an alternative embodiment, the TLR3 agonist is administered by injection. The TLR3 agonists can be applied locally or also to cultured cells (autologous or allogeneic) ex vivo that are then administered to the patient. In particular embodiments, the TLR3 agonist is Polyinosinic:polycytidylic acid (Poly I:C). In other embodiments, hair follicle neogenesis can be stimulated using LL37 alone or in combination with a TLR3 agonist. In addition, common male pattern hair loss can be treated using LL37 alone or in combination with a TLR3 agonist.

The present invention also provides compositions for carrying out the methods described herein. In particular, the present invention provides a composition comprising a TLR3 agonist and a pharmaceutical carrier. In certain embodiments, the TLR3 agonist is a double stranded RNA (dsRNA). In certain embodiments, wherein the TLR3 agonist is Polyinosinic:polycytidylic acid (Poly I:C). In yet another embodiment, a composition comprises LL-37. In particular embodiments, a composition comprises a dsRNA and LL-37.

In other embodiments, the present invention provides a TLR3 agonist for use in a method of stimulating hair follicle neogenesis, in a subject wherein the TLR3 agonist is administered to the subject in a therapeutically effective amount. In a specific embodiment, the present invention provides a dsRNA for use in a method of stimulating hair follicle neogenesis, in a subject wherein the dsRNA is administered to the subject in a therapeutically effective amount. In particular embodiments, the subject has alopecia, is bald, has a wound or has common male pattern hair loss.

Since we demonstrate that dsRNA and TLR3 mediate damage induced responses in the human skin, then our work also directly suggests the use of dsRNA either topically, systemically or in ex vivo cells as a substitute or adjunct to skin conditions where damage mediates benefit. Most notably this includes procedures like dermabrasion and laser resurfacing/ablation/damage for conditions such as aging and photoaging. dsRNA will enhance regeneration in these conditions just as we have shown it does in mice.

DETAILED DESCRIPTION OF THE INVENTION

Figure 1A:
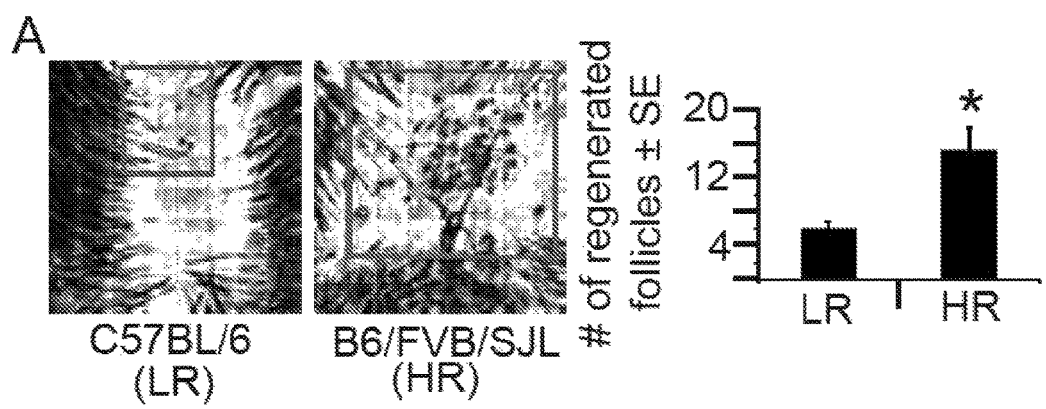
FIG. 1: Tissue damage and double stranded RNA activate TLR3 to promote wound induced hair follicle neogenesis (WIHN). A) Confocal Scanning Laser Microscopy (CSLM) images for C57BL6J (Low Regeneration, "LR") and Mixed B6/FVB/SJL (High Regeneration, "HR") strains of mice. Area of WIHN shown within red box. Original image size is 4 mm2. B) Venn diagram depicting significant overlap between genes associated with high levels of follicle regeneration in mouse skin (in vivo) and human keratinocytes treated with poly (I:C) in vitro published by Karim et al., 2011 under GSE21260. C) Mean fold change in TLR3 mRNA in healed scars at WD20-24 in LR vs. HR mice as determined by qRT-PCR and normalized to housekeeping gene β-actin. D) Mean fold change in TLR3 mRNA four hours post scratch assay in NHEK as determined by qRT-PCR and normalized to housekeeping gene RPLP0. E) WIHN levels in wt mice after standard straight cut or "fringe cut" to wound edge. Area of WIHN shown within red box. Original image size is 4 mm2. F) Photograph at ~WD58-62 of regenerated hair shafts (white, arrows) after poly (I:C) (200 ng) or control injections in WD3 wounds. G) Cross-section H&E histology through the middle of healed scar at WD22 after poly (I:C) (200 ng). Regenerated hair follicles are marked with arrows. Scale bar=500 um. H) WIHN levels in wt mice after poly (I:C) (200 ng) or PBS control measured by CSLM. I) WIHN levels in wt mice after RNase III (15 units) or buffer control measured by CSLM. J) WIHN levels in strain-matched wt control mice and TLR3 KO mice measured by CSLM. K) WIHN in TLR3 KO mice after poly (I:C) (200 ng) compared to PBS control measured by CSLM. *p<0.05 by Student's T-test or Single Factor ANOVA.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Where "about" is used in connection with a number, this can mean the number+/−15%, the number plus 5%, or the number itself without "about." For example, "about 100" would stand for "from and including 85 to and including 115". Where "about" is used in connection with numeric ranges, for example "about 1 to about 3", or "between about one and about three", preferably the definition of "about" given for a number in the last sentence is applied to each number defining the start and the end of a range separately. In certain embodiments, where "about" is used in connection with any numerical values, the "about" can be deleted.

As used herein, the terms "patient", "subject" and "subjects" refer to an animal, preferably a mammal including, but not limited to, a non-primate (e.g., a cow, pig, horse, cat, dog, rat, and mouse) and a non-human primates (e.g., a monkey such as a cynomolgous monkey), and more preferably a human. In a specific embodiment, the subject is a human.

As used herein, the term "effective amount" refers to the amount of an agent (e.g., a prophylactic or therapeutic agent) which is sufficient to cause the desired effect in the particular context, such as stimulate and/or enhance hair follicle neogenesis, stimulate and/or enhance skin regeneration, induce/enhance TLR3 expression/activity in a cell, induce TLR3-mediated signaling in a cell, prevent, reduce or ameliorate the severity, duration and/or progression of a disease or condition or one or more symptoms thereof, ameliorate one or more symptoms of a disease or condition, prevent the advancement of a disease or condition, cause regression of a disease or condition, prevent the recurrence, development, or onset of a disease or condition or one or more symptoms thereof, or enhance or improve the prophylactic or therapeutic effect (s) of another therapy (e.g., prophylactic or therapeutic agent).

The term "specifically binds to" or "selectively binds to" means that a compound (e.g., dsRNA) can bind preferably in a competitive binding assay to the binding partner, e.g., TLR3. Competitive binding assays and other methods for determining specific or selective binding known in the art.

The term "TLR3 agonist" refers to an affinity agent (e.g., a molecule that binds a target molecule) capable of activating a TLR3 polypeptide to induce a full or partial receptor-mediated response. An agonist of TLR3 may induce any TLR3 activity, for example TLR3-mediated signalling, either directly or indirectly. A TLR3 agonist, as used herein, may but is not required to bind a TLR3 polypeptide, and may or may not interact directly with the TLR3 polypeptide. A TLR agonist can also be a small molecule. Examples of TLR3 agonists/enhancers include, but are not limited to, dequalinium dicholoride, ivermectin, entandrophragmin, GW9662, P1,P4-Di(adenosine-5')tetraphosphate triammonium, and astaxanthin.

As employed herein, the phrases "selective TLR3 agonist" and "TLR3 agonist which selectively induces TLR3 activity" refer to compositions which induce TLR3-mediated signalling to a significantly greater extent than signalling by one or more other dsRNA receptors. When the TLR3 agonist is a dsRNA composition, a "TLR3 agonist which selectively induces TLR3 activity" refers to compositions which induce TLR3-mediated signalling to a significantly greater extent than signalling by one or more other dsRNA receptors (e.g., TLR7, RIGI, MDA-5, PKR and/or other dsRNA receptors). In one embodiment, "significantly greater extent," as applied to interaction between TLR3 agonist and a receptor, refers to agonists which have a significantly higher therapeutic index (i.e., the ratio of efficacy to toxicity) for treatment of the target disease state or condition than for activation of pathways mediated by other receptors. The toxicity of therapeutic compounds frequently arises from the non-selective interaction of the therapeutic compound with other receptors. Thus, the present invention provides a means to reduce the incidence of side-reactions commonly associated dsRNA therapy. Preferably, a composition which induces TLR3-mediated signalling to a significantly greater extent than signalling by other another receptor(s) will have an EC50 for induction of TLR3 signalling that is less than the EC50 for signalling by the other receptor(s).

"PolyI", "polyC", "polyA", "polyU", mean polyinosinic acid, polycytidylic acid, polyadenylic acid, and polyuridylic acid, respectively, each optionally substituted with other monomers.

"PolyAU", used interchangeably with "pApU", "polyA:U", poly(A):poly(U), means an at least partially double stranded molecule made of polyadenylic acid(s) and polyuridylic acid(s), each optionally substituted with other monomers so long as the biological function (e.g., immunomodulatory activity, TLR3 agonism or binding) is preserved.

A "homopolymer" is a polymer made of substantially only a single monomer; for example a polyA homopolymer is substantially all A (adenosine) monomers. A homopolymer can be a single longer polymer or can consist of a plurality of shorter polymers concatenated (e.g., using a linker) to form a longer polymer, etc.

A "copolymer" is a polymer made of two or more monomers; for example a poly A copolymer comprises A (adenosine) monomers and one or more monomers other than adenosine.

The term "poly AxU" mean copolymer of adenylic acid and uridylic acid where one uridylic acid is substituted for about every x adenylic acids, respectively. For example "poly C12U" is a copolymer of cytidylic acid and uridylic acid where one uridylic acid is substituted for about every 12 cytidylic acids, respectively.

"dsRNA" and "double-stranded RNA" refer to complexes of polyribonucleotides which are at least partly double stranded. dsRNA need not be double stranded over the length of the molecule, nor over the length of one or more of the single-strand nucleic acid polymers that form the dsRNA. According to the invention, "dsRNA" means double-stranded RNA and is RNA with two partially or completely complementary strands. The size of the strands may vary from 6 nucleotides to 10000, preferably 10 to 8000, in particular 200 to 5000, 200 to 2000 or 200 to 1000 nucleotides. In certain embodiments, the dsRNA is polyinosinic-polycytidylic acid (poly(1:C)), a synthetic analog of dsRNA. Poly(1:C) is composed of a strand of poly(1) annealed to a strand of poly(C). The dsRNA can be a fully or partially (interrupted) pair of RNA hybridized together. It can be made for example by mixing polyinosinic and polycytidylic acid RNA molecules. It also can be made by mixing defined fully or partially pairing non-homopolymeric RNA strands. There is no specific ribonucleotide sequence requirement for the dsRNA molecules to be suitable for preparing a composition of the present invention.

The term "base pair" (abbreviated as "bp") frequently used to indicate the molecular size of nucleic acid is used to indicate the molecular size by the numbers of bases in the nucleic acid (i.e., 10 bp means the double strand polymer having ten bases) in each complementary strand.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "human-suitable" when referring to an agent or composition refers to any agent or composition that can be safely used in humans for, e.g., the therapeutic methods described herein. For example human suitable agents do not cause effects such as severe cytokine induction at a level that would preclude their use in humans, or contain levels of substances (e.g., endotoxins) that are incompatible with use in humans, in the particular context (e.g., mode of administration) in which the agent is used.

An "isolated" or "purified" preparation (e.g., dsRNA preparation) is substantially free of material or other contaminating compounds from the source from which the preparation (e.g., dsRNA) is derived, or substantially free from chemical precursors or other chemicals when chemically synthesized. "Substantially free" means that a preparation of dsRNA is at least 50% pure (wt/wt). In a preferred embodiment, the preparation of dsRNA has less than about 20%, 10%, 5% and more preferably 2% (by dry weight), of free ribonucleotide monomers, proteins or chemical precursors and/or other chemicals, endotoxins, and/or free ssRNA (in the case of a dsRNA preparation), e.g., from manufacture. These also referred to herein as "contaminants". Examples of contaminants that can be present in a dsRNA preparation provided herein include, but are not limited to, calcium, sodium, ribonucleotide monomers, free ssRNA (in the case of a dsRNA preparation), endotoxin, polynucleotide phosphoylase enzyme (or other enzyme having similar substrate specificity), methanol, ethanol, chloride, sulfate, dermatan sulfate, and chondrotin sulfate. Purity and homogeneity are typically determined using analytical chemistry techniques such as polyacrylamide gel electrophoresis or high performance liquid chromatography.

The term "cathelicidins" refers to cationic peptides that have broad-range antimicrobial activity. Zanetti, M. et al. *J. Biol. Chem.* 268, 522 (1993). These peptides belong to the family of anti-microbial peptides which form part of the host's important innate immunity mechanism. Lehrer, R. and T. Ganz. *Curr. Opin. Immunol.* 11, 23 (1999). In humans, cathelicidins and defensins are expressed in immune cells and at epithelial surfaces. See Chromek, M. et al. *Nature Medicine* 12, 636 (2006); Zanetti, M. *J. Leukoc. Biol.* 75, 39 (2004); and Ganz, T. *Nat. Rev. Immunol.* 3, 710 (2003). hCAP18, human cationic antimicrobial protein, with a MW of 18 kD, is the only cathelicidin gene found in humans. Lehrer, R. and T. Ganz. *Curr. Opin. Immunol.* 11, 23 (1999). The N-terminus of this protein consists of a cathelin-like region (similar to the other members of the cathelicidin family) and a C-terminal termed LL-37. See Sorensen, O E. et al. *Blood* 97, 3951 (2001); and Zanetti, M. et al, *FEBS Lett.* 374, 1 (1995), An amphipathic alpha-helical peptide, LL-37 plays an important role in the first line of defense against local infection and systemic invasion of pathogens at sites of inflammation and wounds. Cytotoxic to both bacterial and normal eukaryotic cells, LL-37 is significantly resistant to proteolytic degradation in solution. See Neville, F. et al. *Biophys. J.* 90, 1275 (2006); and Oren, Z., et *Biochem. J.* 341, 501(1999).

Examples of cathelicidins include LL-37/hCAP18 (LL-37) in humans (Curr Drug Targets Inflamm Allergy. 2003 September; 2(3):224-31; Eur J. Biochem. 1996 Jun. 1; 238(2):325-32; Paulsen F et al., J. Pathol. 2002 November; 198(3):369-77). LL-37 is a 37 amino acid residue peptide corresponding to amino acid residue coordinates 134-170 of its precursor hCAP18/human cathelicidin antimicrobial peptide protein (GenBank: Accession NP004336; version NP004336.2 G1:39753970; REFSEQ: accession NM004345.3). LL-37 comprises the amino acid sequence LLGDFFRKSKEKIGKEFKRIVQRIKDFLRN LVPRTES (SEQ ID NO:1). The term LL-37 also includes sequences having at least 90% identity with SEQ ID NO:1. In particular, the term includes sequences having one or more conservative amino acid substittuions of SEQ ID NO:1. Cathelcidins including LL-37 can be used in the methods and composition described herein alone or in combination with dsRNA or other TLR3 agonists to enhance hair follicle neogenesis and/or regeneration.

II. DS-RNA TLR3 Agonist

Double-stranded (ds) RNA (ribonucleic acid) is chemically very similar to DNA (deoxyribonucleic acid). It is also a long molecule containing nucleotides linked together by 3'-5' phoshodiester bonds. Two differences in its chemical groups distinguish dsRNA from DNA. The first is a minor modification of sugar component. The sugar of DNA is deoxyribose, whereas RNA contains ribose, which is identical to deoxyribose except for the presences of an additional hydroxyl group. The second difference is that RNA contains no thymine, but instead contains the closely related pyrimidine, uracil. DsRNA forms from the hyridization of two complementary polyribonucleotides forming a double helix similar to that of DNA. The two strands of the double helix are held together by hydrogen-bonded base pairs.

TLR3 is a receptor for a form of immunity called "innate immunity" which recognizes double-stranded RNAs with a minimum size of at least 50 base pairs. The size requirement or discrimination of dsRNA by TLR3 prevents responses to non-microbial sources of dsRNA micro (mi) RNA or transfer (t) RNA. TLR3 exists as a horseshoe shaped monomer with an N-terminal, ligand-binding extra-cytoplasmic domain (ECD), a transmembrane domain (TMD), and a C-terminal cytoplasmic signaling domain (CSD). X-ray crystallographic studies have provided structural data for the TLR-3 ligand complex which consists of a TLR3 homodimer complexed to dsRNA of at least about 50 consecutive base pairs. The formation of the complex is believed to transmit a conformational change in the CSD via the TMD connector that allows cytoplasmic signaling. Above 50 base pairs, binding affinity is a function of size with a progressive increase in binding affinity with increased length in linear non-branched dsRNA. The minimum size for dsRNA is about 40 nucleotides.

The double-stranded ribonucleic acid (dsRNA) may be fully hybridized strands of poly(riboinosinic acid) and poly (ribocytidilic acid) (i.e., polyIC) or poly(riboadenylic acid) and poly(ribouracilic acid) (i.e., polyAU). If mismatched, the dsRNA may be of the general formula $rI_n \cdot r(C_{4-29}U)_n$, which is preferably $rI_n \cdot r(C_{12}U)_n$, in which r indicates ribonucleotides. It is preferred that n is an integer from about 40 to about 40,000. For example, a strand of poly(riboinosinic acid) may be partially hybridized to a strand of poly(ribocytosinic$_{4-29}$uracilic acid). Other mismatched dsRNA that may be used are based on copolynucleotides such as poly $(C_mU)$ and poly$(C_mG)$ in which m is an integer from about 4 to about 29 or analogs of a complex of poly(riboinosinic acid) and poly(ribocytidilic acid) formed by modifying the $rI_n \cdot rC_n$ to incorporate unpaired bases (uracil or guanine) in the polyribocytidylate $(rC_m)$ strand. Alternatively, mismatched dsRNA may be derived from r(I)r(C) dsRNA by modifying the ribosyl backbone of poly(riboinosinic acid) $(rI_n)$, e.g., by including 2'-O-methyl ribosyl residues. Of these mismatched dsRNA analogs of $rI_n rC_n$, the preferred ones are of the general formula $rI_n \cdot r(C_{11-14}U)_n$ or $rI_n \cdot r(C_{29}, G)_n$ (see U.S. Pat. Nos. 4,024,222 and 4,130,641; which are incorporated by reference). The dsRNA described therein generally are suitable for use according to the present invention. See also U.S. Pat. No. 5,258,369.

The dsRNA may be complexed with an RNA-stabilizing polymer such as polylysine, polylysine plus carboxy-methylcellulose, polyarginine, polyarginine plus carboxymethylcellulose, or any combination thereof. Other examples of mismatched dsRNA for use in the invention include, but are not limited to, $r(I) \cdot r(C_4,U)$; $r(I) \cdot r(C_7,U)$; $r(I) \cdot r(C_{13},U)$; $r(I) \cdot r(C_{22},U)$; $r(I) \cdot r(C_{20},G)$; and $r(I) \cdot r(C_{29},G)$. Mismatched dsRNA may also be modified at the molecule's ends to add a hinge(s) to prevent slippage of the base pairs, thereby conferring a specific bioactivity in specific solvents or aqueous environments which exist in human biological fluids.

Poly-ICLC (interchangeably known as Hiltonol® or poly-IC:LC, among others) is a high molecular weight derivative of poly-IC stabilized with poly L-lysine and carboxymethylcellulose (CMC) that have been added to improve the pharmacokinetic properties of poly-IC. Poly-ICLC therefore has a formula of ln.Cn-poly-1-lysine-5 carboxymethylcellulose. See U.S. Pat. No. 4,349,538. Carboxymethylcellulose is a negatively charged (at neutral pH), hydrophilic material used to maintain the solubility of the complex. PolyICLC is more resistant to nucleases than poly-IC with a 27,000 KDa or larger complex of poly-ICLC being particularly resistant to nucleases.

In specific embodiments, the dsRNA TLR3 agonist is Ampligen®. Ampligen® is a particular dsRNA denoted Poly I: Poly $C_{12}U$, wherein one of the two polyribonucleotides is polyriboinosinic acid and the other is polyribocytidylic$_{12}$, uridylic acid. Thus, the pyrimidine building blocks of Ampligen® are present in a ratio of 12 cytosines of each uracil, while the complementary purine strand contains 13 inosine residues. Within the double-stranded helical structure of Ampligen® the pyrimidine, cytosine, hydrogen bonds with the purine, inosine, while the pyrimidine, uracil, does not form any hydrogen bonds. Therefore, a "mismatch" is created once for every 12 base pairs (bps) formed between the inosine and cytosine residues. In contrast to Ampligen®, Poly I: Poly C contains only complementary inosine: cytosine base pairs. No uracil is present in Poly I: Poly C and there are no mismatches.

Other agonists of TLR3 that may be useful in embodiments of the invention include Poly-ICR (Poly IC (Polyriboinosinic-polycytidylic acid)—Poly arginine (Nventa Biopharmaceuticals Corporation); high MW synthetic dsRNA IPH31XX compounds, for example IPH3102, which in humans are specific for TLR3 (Innate Pharma S. A; Schering-Plough Corporation); Oragens™, for example Oragen™ 0004, Oragen™ 0033 and Oragen™ 0044 (Temple University); and NS9, a complex of polyinosinic-polycytidylic acid (Nippon Shinyaku Co., Ltd). The Oragen™ compounds are synthetic analogues of naturally occurring 2',5'-oligoadenylate analogues, wherein the analogues are typically conjugated to a carrier molecule to enhance cellular uptake (see U.S. Pat. No. 6,362,171).

PCT Publication No. WO 2009/130616 (Innate Pharma) describes high MW polyAU dsRNA molecules that are TLR3 agonists. PCT Publication Nos. WO 2006/054177, WO 2006/054129, WO 2009/130301 and WO 2009/136282 (Institut Gustave Roussy) describe the use of dsRNA TLR3 agonists for treating cancer.

Further embodiments are also disclosed in WO 2007/089151, which describes stathmin and stathmin-like compounds that are TLR3 agonists. In a specific embodiment, a nucleic acid-based agonist is coupled to one of these stathmin or stathmin-like agonists.

In another embodiment, the dsRNA TLR4 agonist is rugged dsRNA. Rugged dsRNA is a novel form of dsRNA with a unique composition and physical characteristics. Unlike the previously known antiviral, Ampligen® (Poly I: Poly $C_{12}U$), the new and improved form of Rugged dsRNA (e.g., Poly I: Poly $C_{30-35}U$ (preferably, Poly I: Poly $C_{30}U$), wherein Poly$C_{30-35}U$, indicates a ratio, that is, that for every U there are 30-35 C's), has an increased Ruggedness characterized by an increase resistance to thermal denaturation and ribonuclease digestion. This improved form of dsRNA also has a reduced tendency to form branched dsRNA molecules which results in increased bioactivity due to an increased ability to bind TLR3 receptor. The minimal length of Rugged dsRNA (termed the monomer unit) is about 50 base pairs requiring about 4 to 5 (e.g., 4.7) helical turns (10.7 base pairs are required for each complete turn of the helix) within its dsRNA structure and represents the smallest or monomeric unit of Poly I: Poly $C_{30}U$, approximately 24,000 to 30,000 Daltons (a Dalton is a unit of weight equal to the weight of a single hydrogen atom). The maximal length of Rugged dsRNA is about 500 base pairs composed of about 10 monomer units, requiring about 50 (e.g., 46.7) helical turns and having a molecular weight of approximately 300,000 Daltons (e.g., about 225,000 Daltons). See U.S. Patent Application Publication No. 20120009206.

III Formulations and Pharmaceutical Compositions

In a preferred embodiment, the compositions comprising a TLR3 agonist are administered topically. It is preferable to present the active ingredient, i.e. TLR3 agonist as a pharmaceutical formulation. Exemplary compositions are described in detail in the examples which follow. The active ingredient may comprise, for topical administration, from 0.001% to about 20% w/w, by weight of the formulation in the final product, although it may comprise as much as 30% w/w, from about 1% to about 20% w/w of the formulation. The topical formulations of the present invention, comprise an active ingredient together with one or more acceptable carrier(s) therefor and optionally any other therapeutic ingredients(s). The carriers must be "acceptable" in the sense of being compatible with the other ingredients of the formulation and not deleterious to the recipient thereof.

The TLR3 agonist composition of the present invention can be administered to a patient either by itself or in pharmaceutical compositions where it is mixed with suitable carriers or excipient(s). In treating a patient exhibiting a disorder of interest, a therapeutically effective amount of an agent or agents such as these is administered. A therapeutically effective dose refers to that amount of the compound that results in amelioration of symptoms or a prolongation of survival in a patient.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, capsules, or solutions. The pharmaceutical compositions of the present invention may be manufactured in a manner that is itself known, e.g., by means of conventional mixing, dissolving, granulating, emulsifying, encapsulating, entrapping or lyophilizing processes.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment with topical formulations of TLR3 agonist, in other aspects of the invention TLR3 agonist might be delivered by other methods. For example, TLR3 agonist might be formulated for parenteral delivery, e.g., for subcutaneous, intravenous, or intramuscular injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form.

Formulations suitable for topical administration include liquid or semi-liquid preparations suitable for penetration through the skin to the site of where treatment is required, such as liniments, lotions, creams, ointments or pastes. Lotions according to the present invention include those suitable for application to the skin. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methyl-cellulose, and/or polyvinyl pyrrolidone (PVP). If desired, disintegrating agents may be added, such as the cross-linked polyvinyl pyrrolidone, agar, or alginic acid or a salt thereof such as sodium alginate.

For preferred topical delivery vehicles the remaining component of the composition can be water, which is necessarily purified, e.g., deionized water. Such delivery vehicle compositions can contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components.

Other known transdermal skin penetration enhancers can also be used to facilitate delivery of a TLR3 agonist. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle. Indeed, onne skilled in the art can easily determine the appropriate dose, schedule, and method of administration for the exact formulation of the composition being used, in order to achieve the desired effective amount or effective concentration of the agent in the individual patient.

The dose of a presently disclosed composition, administered to an animal, particularly a human, in the context of the presently disclosed subject matter should be sufficient to produce at least a detectable amount of a therapeutic response in the individual (e.g., stimulate hair follicle neogenesis) over a reasonable time frame. The dose used to achieve a desired effect will be determined by a variety of factors, including the potency of the particular agent being administered (e.g., a TLR3 agonist), the pharmacodynamics associated with the agent in the host, the severity of the condition in the subject, other medications being administered to the subject, the degree of susceptibility of the individual, the age, sex, and weight of the individual, idiosyncratic responses of the individual, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Accordingly, in certain embodiments, the compositions can be administered/applied at a dose of about 1-100 µg/cm$^2$ including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/cm$^2$ area per application.

In a more specific embodiment, the compositions can be administered/applied in a range of about 1-20 µg/cm$^2$ area per application including, but not limited to, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, and 19-20 µg/cm$^2$ area per application.

The pharmaceutical compositions can be administered on a daily basis. In one embodiment, the compositions are administered once a day for 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks or more including 1, 2, 3, 4, 5, 6, 7, 8, 9, 10, 11, or 12 months.

The compositions can be administered once every few days including once every 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The compositions can be administered once a week for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more. Alternatively, the compositions can be administered once every few weeks for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more.

In other embodiments, the compositions can be administered several times in a month including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 times per month.

In particular embodiments, the dose of a composition described herein comprises a range of about 2-10 µg/cm$^2$ area per application, with 1-10 applications separated within one month. In other embodiments, the dosage is about 2-10 µg/cm$^2$ area per application, with 1-3 applications separated within one month.

In certain embodiments, the presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising the presently disclosed compounds. Alternatively, these agents may be part of a single dosage form, mixed together with one or more presently disclosed compounds in a single composition.

By "in combination with" is meant the administration of one or more presently disclosed TLR3 agonists with one or more therapeutic agents either simultaneously, sequentially, or a combination thereof. Therefore, a cell or a subject can receive one or more TLR3 agonists and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the one or more TLR3 agonists and one or more therapeutic agents are administered simultaneously, they can be administered to the cell or administered to the subject as separate pharmaceutical compositions, each comprising either one or more presently disclosed compounds or one or more therapeutic agents, or they can contact the cell/subject as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Wound Induced Hair Neogenesis (WIHN). All animal protocols are approved by the Johns Hopkins University Animal Care and Use Committee. C57BL/6J, B6; 129SF2/J and TLR3 null mice (B6; 129S1-Tlr3tm1Flv/J) were obtained from The Jackson Laboratory. Mixed strain (C57BL/6J×FVB/N×SJL/J) animals were provided by Dr. Jean Richa (University of Pennsylvania).

A 1 cm2 excisional full-thickness wounds to the level of skeletal muscle on the backs of 21-day old male and female mice was performed as previously described (Ito et al., 2007; Nelson et al., 2013). Numbers of regenerated hair follicles were quantified in the re-epithelialized skin by non-invasive confocal scanning laser microscopy (CSLM) as published (Fan et al., 2011). For all experiments, 504 of "intervention" was injected into healing wound (under scab) or applied topically into open wound as shown in Table 1 below.

| Experiment | Mouse Strain | # of Mice | Intervention | Day of Intervention | Day of CSLM Assessment |
|---|---|---|---|---|---|
| High vs Low Gene Expression-Early; High vs Low Gene Expression-Late | C57 vs. C57 × FVB × SJL C57 × FVB × SJL | 4 mice per strain; 3 mice/group | none | | wound closure; ~WD20- |
| Standard WIHN vs Fringe Cuts | C57BL/6J | 14-15 mice/group | 10 cuts/side | WD0 | ~WD20-24 |
| Poly (I:C) | C57 × FVB × SJL; B6;129S1-Tlr3tm1Flv/J | 10-11 mice/group; 9 mice/group | 200 ng Poly IC injected into wound | WD3 | ~WD20-24 |
| Rnase III | C57 × FVB × SJL | 17-19 mice/group | 15 units Rnase III topically applied to wound | WD2-3 | ~WD20-24 |
| WIHN in TLR3 KO | B6; 129S1-Tlr3$^{tm1Flv/J}$; B6; 129SF2/J | 6 mice/group | none | — | ~WD20-24 |
| IL-6 | C57BL/6J | 30 mice/group | 25 ng rmIL-6 protein injected into wound | WD7 | ~WD20-24 |
| Cucurbitacin I | C57BL/6J | 10-14 mice/group | 2 mg/kg cucurbitacin I injected into wound | WD7 | ~WD20-24 |

Cell Culture. Neo-natal human epidermal keratinocytes (Lonza, Walkersville, Md.) or lab-isolated foreskin keratinocytes were cultured in keratinocyte medium with added supplements (KGMGOLD). Treatment with recombinant IL-6 protein (50 ng/mL), cucurbitacin I (10-100 nM), poly (I:C) (20 μg/mL) and TLR3 pharmacological inhibitor (80 μM; EMD Millipore, Billerica, Mass.) was applied in basal medium containing transferrin, hydrocortisone and antibiotics for up to 24 hours. After 24 hours, treatment medium was replaced with KGM-GOLD and isolation of RNA as indicated.

Nucleofection. Nucleofection with siGENOME SMARTpool Human Tap63, TLR3, REL-A and siCONTROL siRNA duplex oligonucleotides (Dharmacon-ThermoFischer Scientific) was performed in NHEK using the Amaxa 4D-Nucleofector according to manufacturer's instruction. Plated cells were treated with recombinant human IL-6 (50 ng/mL) protein or poly(I:C) (20 μg/mL) for 24 hours. Afterwards, treatment medium was removed and replaced with KGMGOLD complete medium for the duration of the experiment. Levels of appropriate gene expression were assessed by qRT-PCR using inventoried TaqMan reagents in three independent experiments.

Gene Expression Analysis. RNA from immediately re-epithelialized skin at ~12 days after wounding (early stage) or after the earliest time point of hair follicle detection by CSLM (late stage; ~16 days) was submitted the JHMI Deep Sequencing & Microarray core for Affymetrix® Mouse Exon 1.0ST microarray chips according to manufacturer's protocols. Raw gene expression signals in the form of Affymetrix CEL files were extracted and normalized with Partek® Genomics Suite™ software using the Robust Multichip Analysis (RMA) algorithm (Irizarry et al., 2003). The Student's t-test ANOVA was used to detect genes with significantly different expression. These analyses have been submitted to the Gene Expression Omnibus database (under GSE50418 and GSE50419; http://www.ncbi.nlm.nih.gov/geo/).

Quantitative Real-Time PCR (qRT-PCR). Mouse skin was harvested prior to wounding and throughout wounding as described (Nelson et al., 2013). RNA was isolated from NHEK with RNeasy Mini Kit (Qiagen, Valencia, Calif.) with DNase I digestion. qRT-PCR was performed for genes of interest and 18S or ribosomal protein, large PO (RPLP0) (housekeeping genes) using inventoried TaqMan reagents. Differences in gene expression were assessed by comparative $\Delta\Delta C_T$ values with fold change calculations.

ELISA. IL-6 protein levels were assayed by ELISA (R&D Systems, Minneapolis, Minn.) nonwounded and from and wounded skin or healed mouse scars at times indicated. A minimum of three independent mice were used for each time point.

Immunohistochemistry, Immunocytochemistry and Histology. Immunohistochemistry was performed on formalin-fixed paraffin-embedded mouse skin samples using the avidin-biotin complex method and AEC development (Vector Laboratories). Indicated antibodies were applied overnight. Sections were counterstained with hematoxylin. Images were captured at 40× magnification using a Nikon Optiphot microscope and Nikon Elements F software. Histology was assessed by H&E after IL-6 addition. The epidermal thickness from the basal layer keratinocytes to beginning of stratum corneum in three locations per healed mouse wound in multiple histology sections was measured by Image J software.

Immunocytochemistry was performed on NHEKs plated on plated on collagen-coated coverslips and treated with 20 mg/ml poly (I:C) as above. Fixed cells were incubated with primary antibodies overnight, appropriate Alexa Fluor secondary antibodies and counterstained using VectaShield DAPI mounting medium (Vector Labs, Burlingame, Calif.). Slides were imaged at 60× magnification using the Nikon C1si True Spectral Imaging Confocal Laser Scanning Microscope system (Cell Imaging Core Facility, Sidney Kimmel Comprehensive Cancer Center, Johns Hopkins, Baltimore, Md.). Cell morphology and beta-catenin nuclear localization were quantified using the CellProfiler image analysis software (www.cellprofiler.org) (Carpenter et al., 2006) from confocal images of nuclei.

Flow Cytometry. Keratinocytes and fibroblasts were fixed, permeabilized (BD Cytofix/Cytoperm kit), and stained with antibodies against human vimentin (BD Pharmingen clone RV202) and KRT15 (Abam clone LHK15) labeled with a chromophore preconjugated to Fab (Zenon mouse IgG labeling kit). Data was collected on a dual-laser flow cytometer (BD FACSCalibur) followed by FlowJo 10 (TreeStar) software analysis.

To measure TCRγδ expression, healed wounds (~WD20) from wild type and TLRKO3 mice were minced and digested at 37 C in a buffer containing RPMI 1640, 1.67 collagenase Wunsch units/mL Liberase TL (Roche Life Sciences, Indianapolis, Ind.) and 0.01% DNAse (Sigma—Aldrich, St Louis, Mo.) for 75 minutes. Following digestion, samples were washed and filtered (40 µm) to obtain a single cell suspension. Cells were stained with propidium iodide (Miltenyi Biotec, San Diego, Calif.) and TCRγδ (GL3) antibody (Miltenyi Biotec, San Diego, Calif.) followed by analysis with MACSQuant cytometer and FlowJo software.

Chromatin Immunoprecipitation. Poly(I:C) treated and control keratinocytes were crosslinked in 1% formaldehyde for 10 minutes, followed by addition of glycine for 5 minutes to quench unreacted formaldehyde. Cells were processed with EZ-ChIP Kit (Millipore) according to the manufacturer's instructions. Crosslinked protein-DNA complexes were captured with rabbit anti-Stat3 or normal rabbit IgG (sc-482X; sc-2027X, SCBT) antibodies. Real-time quantitative PCR was performed to determine the relative abundance of the promoter DNA sequence, associated with Stat3. Primers are detailed in Expanded Experimental Methods. Primers and graphics were designed based on ENCODE data (UCSC Genome Browser).

Statistical Analysis. Each experiment was repeated with at least 3 independent litters of animals or keratinocyte cultures. Data was analyzed using Student's t-test or ANOVA Single Factor. Statistical significance was considered at $*p<0.05$.

Reagents and Primer Sets:

Antibodies. Rabbit polyclonal antibodies to phosphorylated Stat 3, Stat3, Ki-67, cleaved caspase 3, β-actin and secondary anti-rabbit HRP were obtained from Cell Signaling Technology (Danvers, Mass.). Anticytokeratin 1 (Krt1), rabbit IL-6, KRT15 (LHK15) and pan-cadherin antibodies was obtained from Abcam (Cambridge, Mass.). Mouse monoclonal β-catenin antibody (14) and vimentin (RV202) were obtained from BD Biosciences (San Jose, Calif.) and rabbit polyclonal keratin 5 antibody was purchased from Covance (Princeton, N.J.). FITC-Phalloidin was obtained from Sigma (St Louis, Mo.). Mouse and rabbit IgG isotype controls were purchased from Invitrogen (Camarillo, Calif.).

Treatments during WIHN assay. Recombinant mouse IL-6 protein (R&D Systems, Minneapolis, Minn.) and poly (I:C) (High Molecular Weight; InVivogen, San Diego, Calif.) was diluted in sterile PBS immediately prior to injection. Cucurbitacin I (Tocris Biosciences/R&D Systems, Minneapolis Minn.) was dissolved in 10% EtOH/PBS to a final concentration of 1 mg/mL prior to injection. RNase III enzyme (Life Technologies, Grand Island N.Y.) was diluted in supplied reaction buffer ChIP. The amplicon for Gli2 promoter site 4 encompasses TTCCAGGAA (SEQ ID NO:2) on chr2: 121621123-121621782 in the Encode database. It was amplified with the primer sequences: a) forward: 5 VACAGATAAGCTGAGT-CACAGGA3' (SEQ ID NO:3); b) reverse: 5'TCCTGTTCA-CATTGACGCC3' (SEQ ID NO:4). The amplicon for β-catenin promoter site 4 encompasses TTCCTGGAA (SEQ ID NO:5) on chr3: 41264037-41264357 in the Encode database. This was amplified with the primer sequences: a) forward: 5'TGCCTTTGCATCAACAACAAGG3' (SEQ ID NO:6); b) reverse: 5'TCAGAAACCAACTGGTCAT-GTCT3' (SEQ ID NO:7).

Results

Figure 1B:
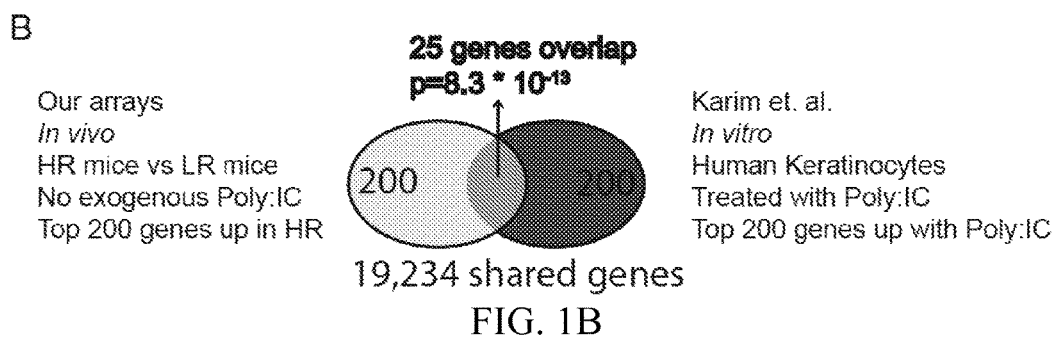
Figure 1C:
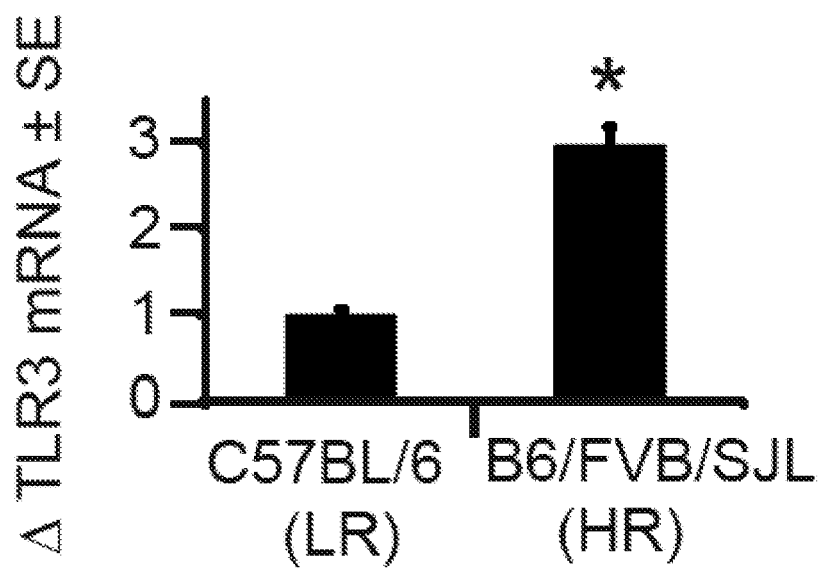
Figure 8A:
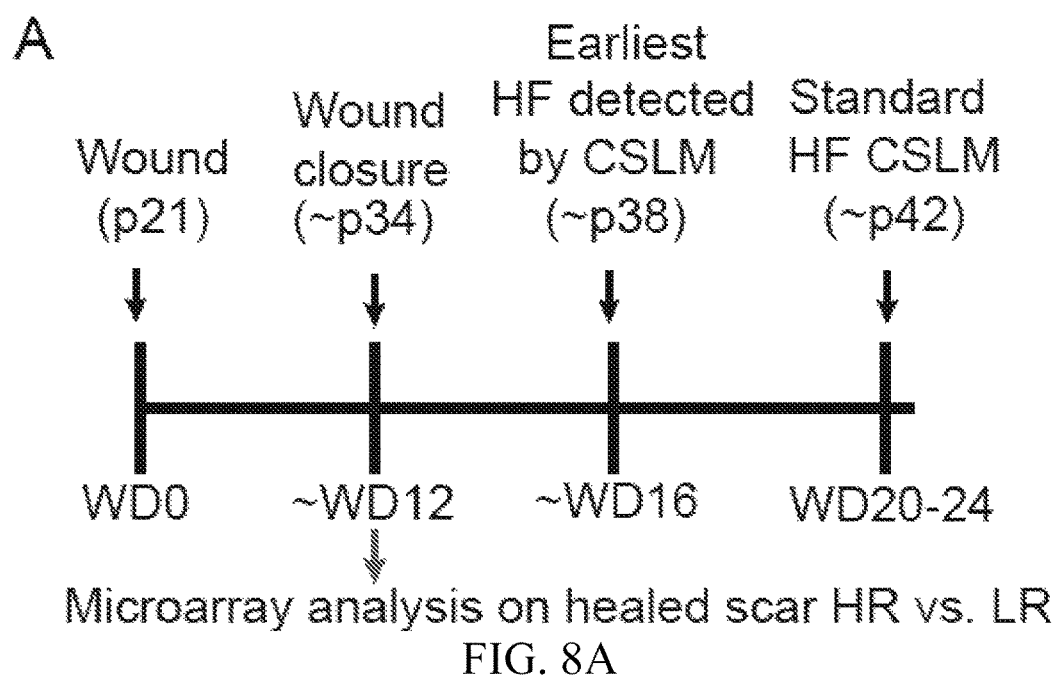
FIG. 8: Microarray analysis at wound closure but prior to regeneration indicates TLR3 signaling signature. A) Microarray analysis was performed on healed scars at the earliest time of wound closure and reepithelialization, prior to morphogenesis (~WD 12) on Low Regenerating (LR) and High Regenerating (HR) strains of mice. B) 25 Genes of overlap from FIG. 1B between top 200 genes in HR mice and top 200 genes in dsRNA treated keratinocytes from Karim et al. Fold changes and p-values are from mouse array. Genes in bold are associated with dsRNA recognition or induced by interferon, known TLR3 effects. C) Time course of TLR3 mRNA expression throughout early stage wound healing in wt mice, normalized to housekeeping gene, β-actin, as determined by qRT-PCR. D) Wound closure and healing were monitored daily in strain-matched control and TLR3 null mice and average day of scab detachment (SD) as an indication of epithelialization. E) Representative image of non-wounded murine skin after control or poly (I:C) injection (200 ng/mouse) during telogen showing no activation of anagen.
Figure 8C:
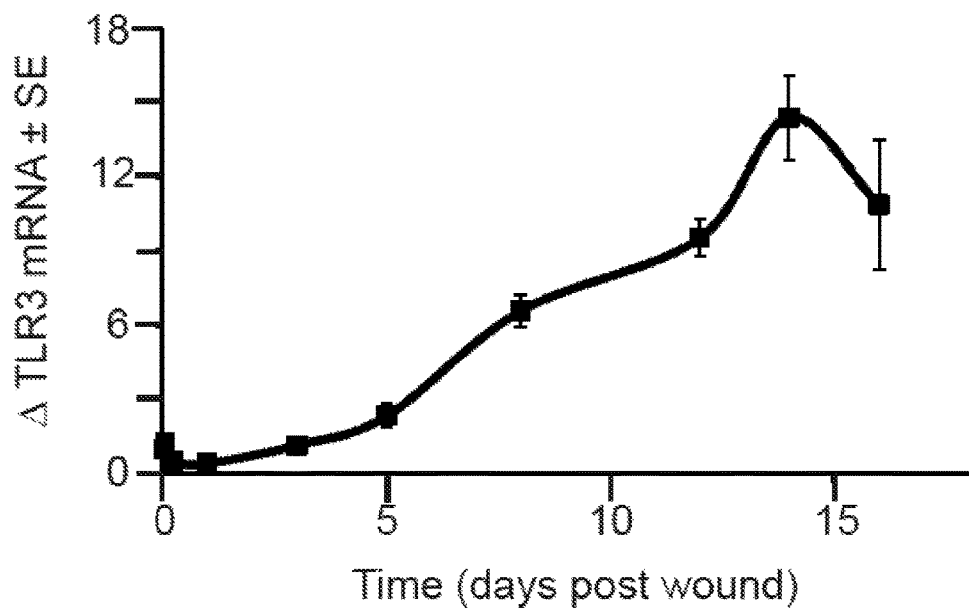

Hair follicle regeneration after wounding recapitulates embryonic follicle development in both morphogenic and molecular detail. However, the events that dictate whether wound healing proceeds by regeneration or fibrotic scarring remain unclear. In studies characterizing molecular mechanisms of WIHN, we and others observed significant differences in the regenerative capacity of various mouse strains when visualized by confocal scanning laser microscopy (CSLM) (FIG. 1A) (Fan et al., 2011; Ito et al., 2007; Nelson et al., 2013). To identify factors that may initiate regeneration, we compared gene expression profiles from healed wounds of mice with high and low regenerative capacity using C57BL/6 and our mixed background strain of mice (C57BL/6×FVB×SJL). This analysis was performed at the time of wound closure but before the onset of hair morphogenesis to enrich for upstream factors in the WIHN pathway (FIG. 8A, Materials and Methods). Ingenuity Pathway Analysis identified "viral pattern recognition receptors" and "interferon-signaling" as the most significantly up-regulated pathways in highly regenerative mice.

dsRNA released by tissue damage activate TLR3 to Promote Regeneration. We focused on the pattern recognition receptor TLR3, which is activated by dsRNA and known to induce interferon signaling (Uematsu and Akira, 2007). The TLR3 gene expression pattern we observed in highly regenerative murine skin wounds showed strong overlap with the pattern obtained from human keratinocytes treated with the synthetic dsRNA mimic poly (I:C) (FIG. 1B) (Karim et al., 2011). Strikingly, despite the differences in species and experimental conditions, 25 of the 200 most highly up-regulated genes were common to both analyses (FIG. 8B). This observed overlap in expression of genes involved in dsRNA-sensing suggested a potentially conserved role for TLR3 in early wound healing responses. Furthermore, expression of TLR3 itself was 3-fold higher in our highly regenerative mouse strain as observed by qRT-PCR, validating the expression patterns observed in the array analyses (FIG. 1C).

Figure 1D:
Figure 1E:
Figure 1E:
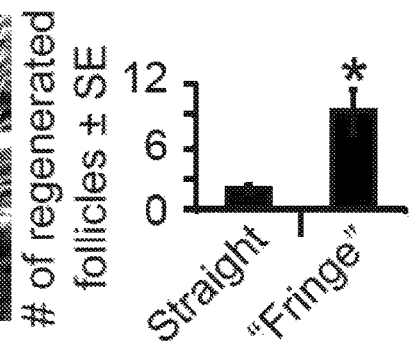
Figure 1F:
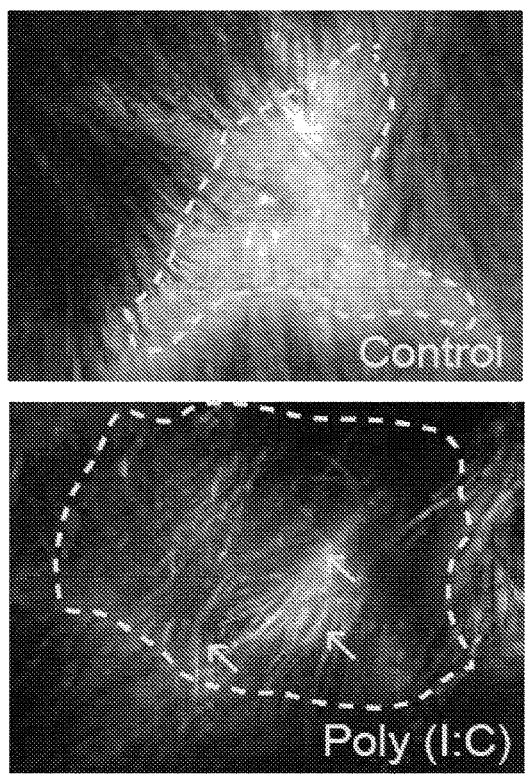
Figure 1G:
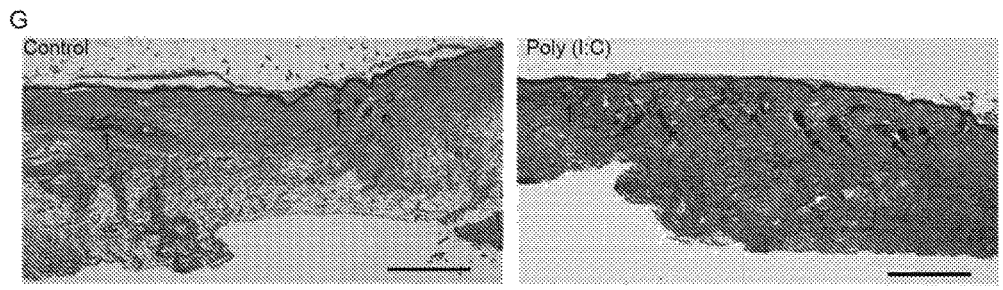
Figure 1H:
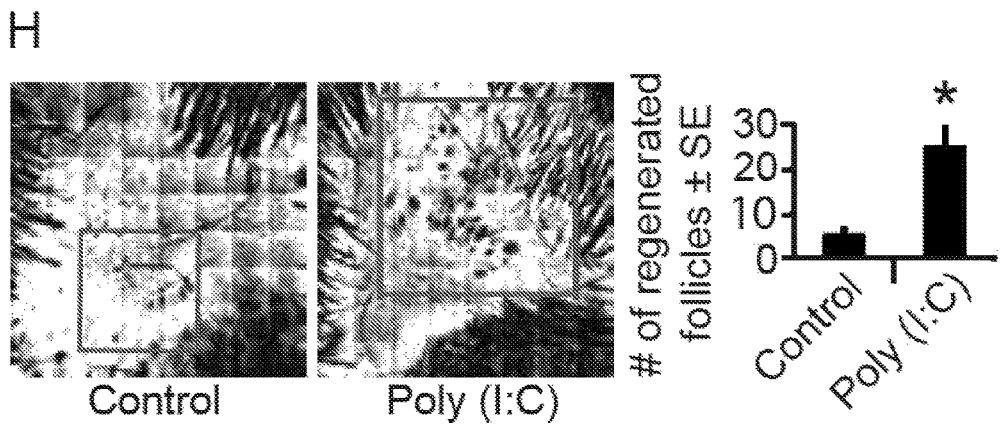
Figure 1I:
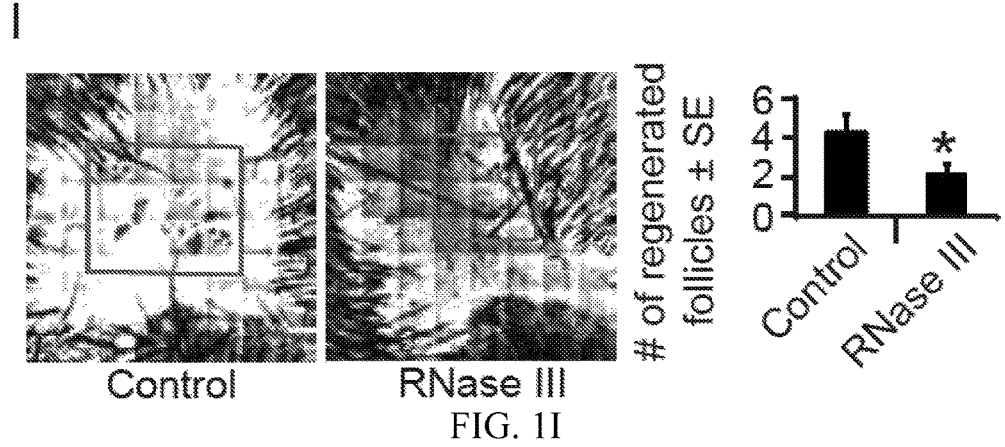
Figure 1J:
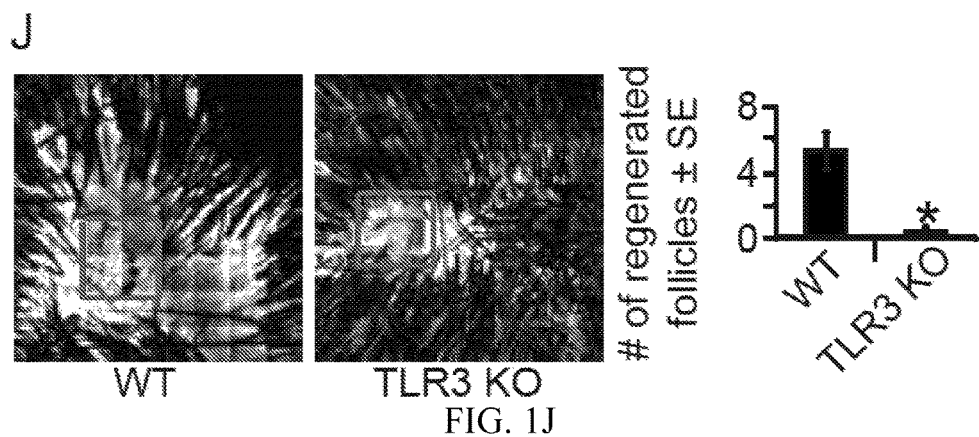
Figure 1K:
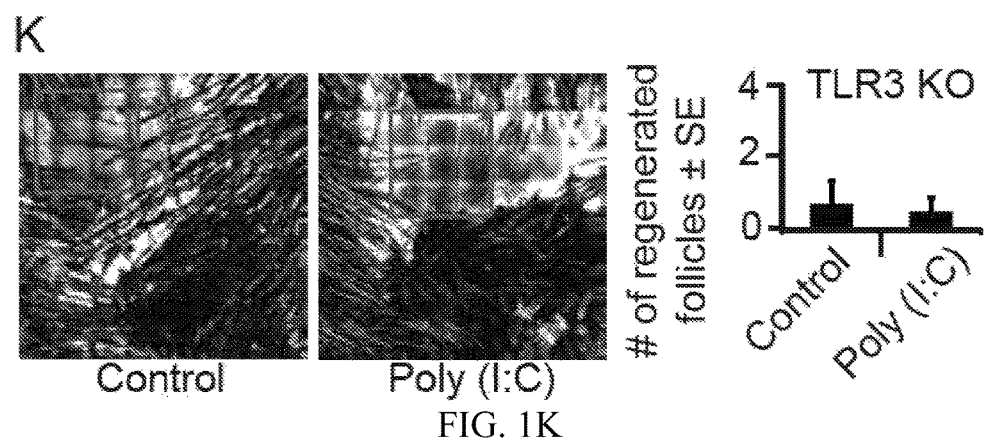
Figure 8D:
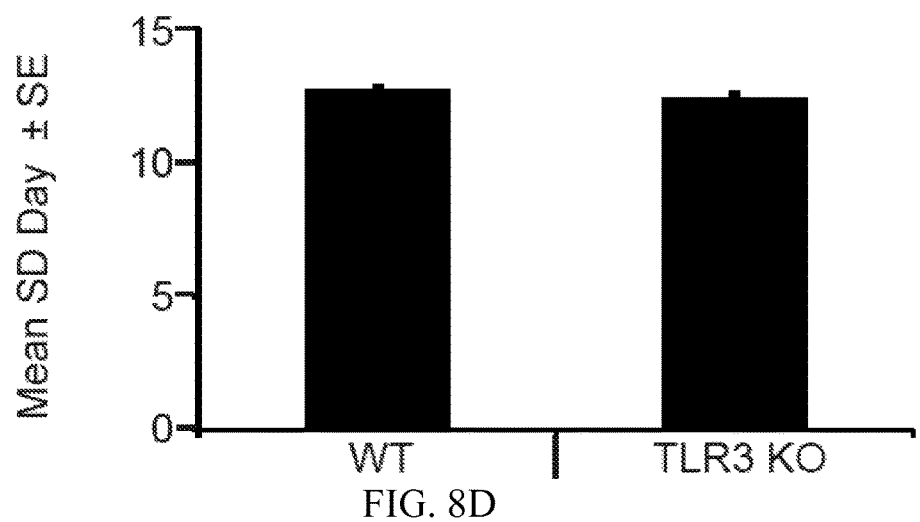
Figure 8E:
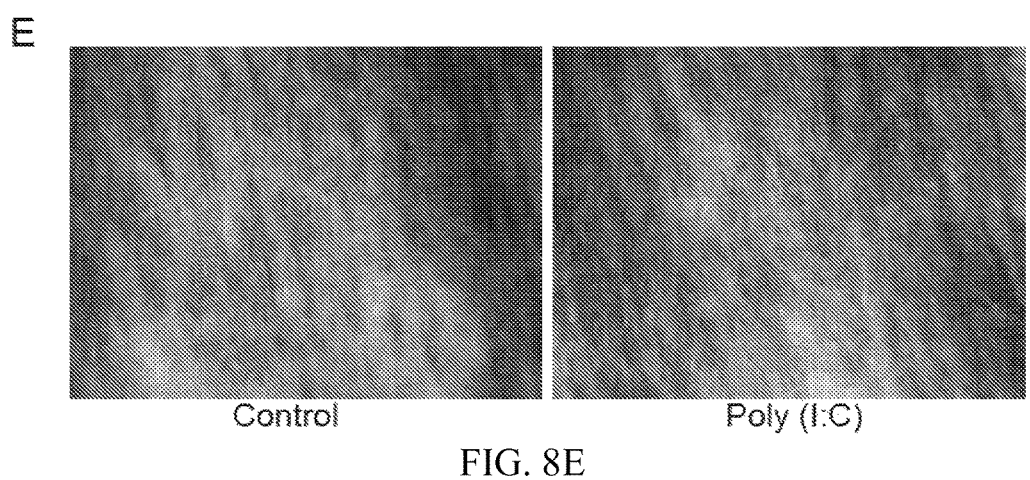

In previous studies, TLR3 mRNA was induced in response to dsRNA released during wounding (Bernard et al., 2012). This suggested to us that during WIHN, TLR3 may serve as a positive-feedback sensor of tissue damage, consistent with an upstream role in the regeneration process. In support of this hypothesis, TLR3 expression is significantly elevated in healing wounds five days after wounding and continues to increase throughout the healing process (Supp. FIG. 1C). We also examined TLR3 expression following scratching of human keratinocytes in culture. TLR3 expression was nearly 5-fold higher in scratched keratinocytes compared to unmanipulated controls (FIG. 1D). Furthermore, increasing the extent of damage during wounding in vivo by placing minute perpendicular cuts at the wound edge significantly increased the number of regenerated follicles (FIG. 1E, Methods). We next explored whether augmenting the natural dsRNA release during wounding could lead to an increase in regeneration. Indeed, a single addition of the dsRNA mimic poly (I:C) into murine skin wounds led to a greater number of regenerated follicles (FIG. 1F-H) Conversely, addition of the dsRNA-specific endonuclease RNase III significantly decreased the number of regenerated follicles (FIG. 1I) To confirm that the effects of dsRNA on WIHN are TLR3-dependent, we next examined the extent of regeneration in TLR3 null mice. Impressively, regeneration was almost completely abolished in these mice compared to strain-matched controls, despite their comparable re-epithelialization kinetics (FIG. 1J; FIG. 8D). Moreover, the stimulatory effect of dsRNA on WIHN was abrogated in TLR3 null mice, demonstrating the necessity of TLR3 for damage-induced regeneration (FIG. 1K). However, poly (I:C) does not affect the hair cycle in normal nonwounded murine skin (FIG. 8E). Together, these data suggest that TLR3 activation by dsRNA released during wounding initiates regeneration.

Figure 2A:
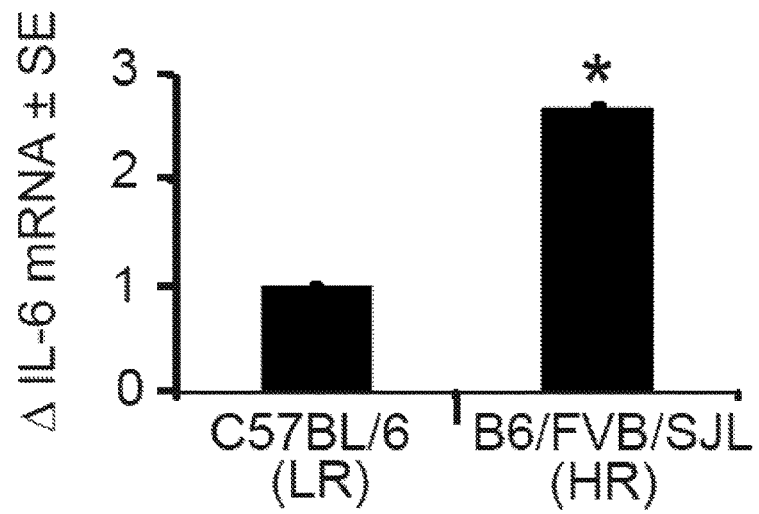
FIG. 2: IL-6 and pSTAT3 mediate TLR3 effects on WIHN. A) Mean fold change in IL-6 mRNA in healed scars at WD20-24 in HR vs. LR strains of mice as determined by qRT-PCR and normalized to housekeeping gene β-actin. B) Mean fold change in IL-6 mRNA after poly (I:C) addition (20 μg/mL) to NHEK for 6 hours or in strain matched wt and TLR3 KO mice 6 hours after wounding as determined by qRT-PCR and normalized to housekeeping gene RPLP0 (NHEK) or β-actin (mouse). C) Time course of IL-6 mRNA and protein expression throughout early stage wound healing in wt mice, as determined by qRT-PCR and ELISA, respectively. D) IL-6 (middle panels) and P-STAT3 (right panels; arrows) immunohistochemistry of healing scars at WD5 and WD8 in wt mice. Scale bar=50 μm. E) Cross-section histology of healed scar at WD22 after a single injection of IL-6 (25 ng) or PBS control at WD7. Regenerated hair follicles are marked with arrows. Scale bar=100 μm. F) Regenerated hair shafts (white, arrows) at ~WD58-62 as visualized by dissecting microscope. G) WIHN in wt mice after single dose of rmIL-6 (25 ng) compared to PBS control as measured by CSLM. H) WIHN levels in wt mice after cucurbitacin I (2 mg/kg) or control as measured by CSLM. I) P-STAT 3 levels in the presence of cucurbitacin I (+) compared to control (−) in wt mice as measured by western blot and normalized to STAT3. PC=P-STAT3 positive control cell lysate. *p<0.05 by Student's T-test or Single Factor ANOVA.
Figure 2B:
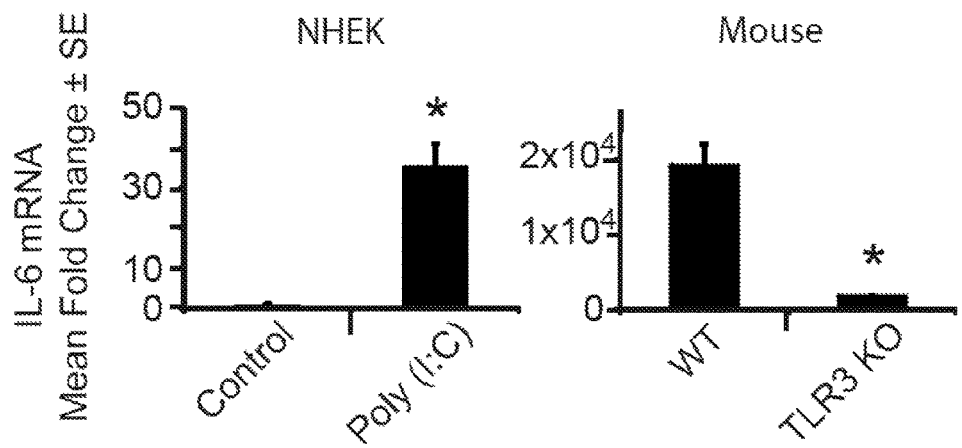
Figure 2C:
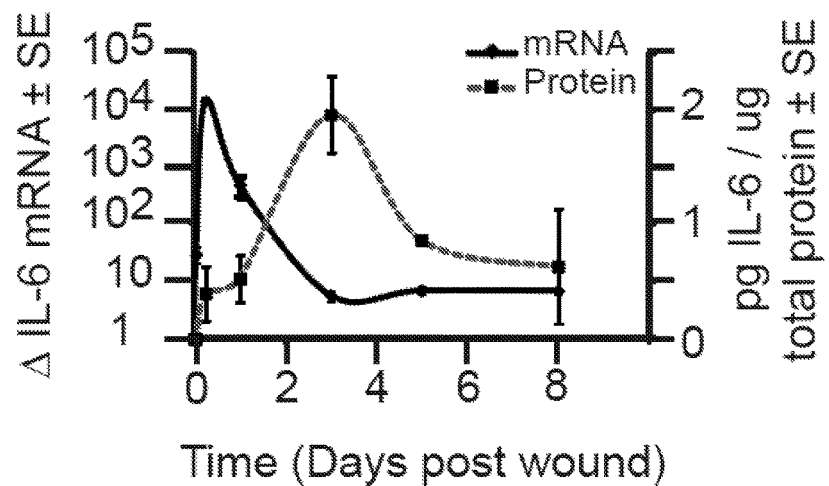
Figures 9A, 9B:
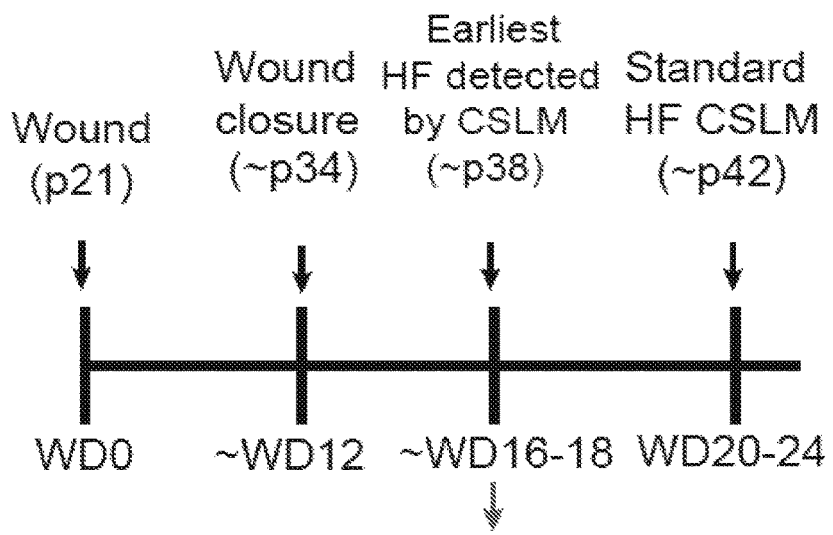
FIG. 9: Gene expression analysis and qRT-PCR verification of gene expression changes on late stage microarrays. A) Microarray analysis was performed on healed scars at WD16 on three LR and HR mouse scars as indicated. B) Signaling pathways enriched and selected changed genes in samples with high regeneration. C) Top 5 genes associated with enriched signaling pathways in 1B. D) Selected significantly changed interleukins, chemokines, and cytokines in HR. E) Top gene ontology "functions" enriched in HR. F) qRT-PCR verification of microarray gene expression of selected genes: Interleukin 6 (IL-6); interleukin 10 (IL-10), forkhead box protein P3 (Foxp3). Data represent the Mean±SE of the fold change in gene expression; n=5-10; *p<0.05 G) Mean fold change in IL-6 mRNA 24 hours post scratch assay in NHEK as determined by qRT-PCR and normalized to housekeeping gene, RPLP0. H) Mean fold change in IL-6 mRNA with RelA-specific or scrambled control siRNA in the presence of poly (I:C) (20 μg/mL) in keratinocytes as determined by qRT-PCR and normalized to housekeeping gene, RPLP0.
Figures 9E, 9F:
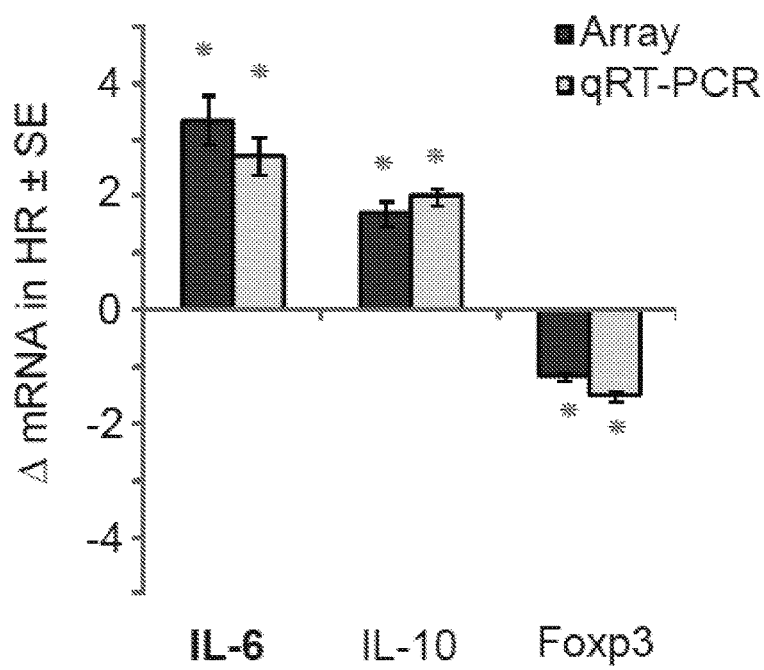
Figure 9G:
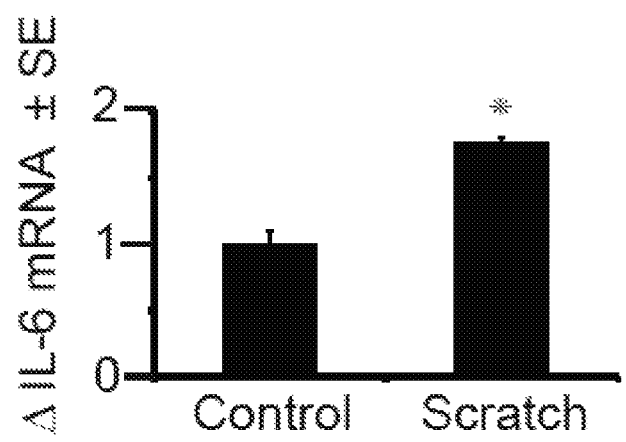
Figure 9H:
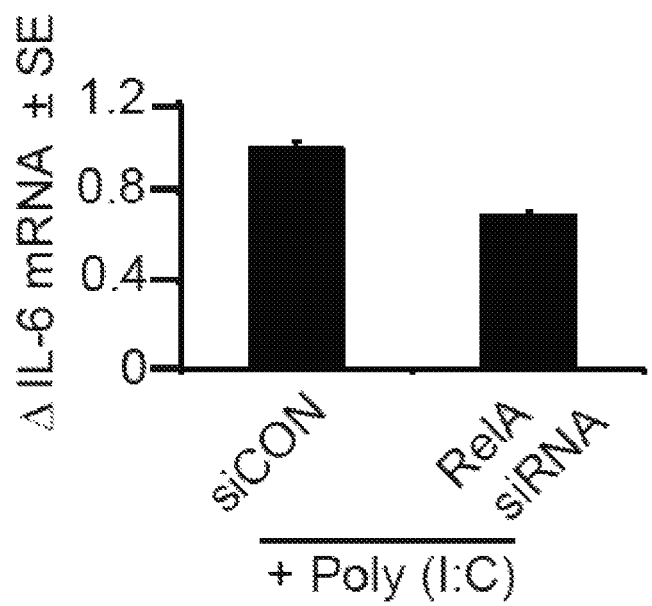

TLR3 effects on regeneration are mediated by IL-6 and pSTAT3. To examine the mechanism by which TLR3 promotes regeneration, we performed gene expression analysis on mice at 16 to 18 days post-wounding (WD16-18), later than the array above, and at the earliest time points at which regenerated follicles can be detected by CSLM (FIG. 9A). Gene expression from healed wound beds of animals with robust regeneration (average 49 hair follicles) were compared to those of animals that failed to regenerate hair follicles, revealing up-regulation of several interleukins and cytokines in more highly regenerative mice. Of particular interest were interleukin-6 (IL-6) and its pathway components as well as TLR3 itself, which appeared as the top upstream regulator of IL-6 in this analysis (FIG. 9B-F). Just as we had found for TLR3, mixed strain animals with high regenerative capacity had 3-fold higher levels of IL-6 compared to C57BL/6 mice with poor regeneration (FIG. 2A). These data led to the hypothesis that IL-6 may mediate the effects of TLR3 on regeneration. TLR3 has previously been demonstrated to induce IL-6 in a dsRNA dependent manner (Melkamu et al., 2013) and IL-6 is a known activator of regeneration in other contexts, particularly in response to liver damage (Galun and Rose-John, 2013; Jia, 2011). Consistent with this, just as TLR3 expression is increased within injured (scratched) keratinocytes in culture, IL-6 mRNA also increased (FIG. 9G). In keratinocytes treated with poly (I:C), we observed a greater than 30-fold induction of IL-6 mRNA (FIG. 2B), which is partially mediated through the downstream transcription factor, NFκB (FIG. 9H). This induction is TLR3-dependent as TLR3−/− animals had far less IL-6 mRNA after wounding than strain-matched controls (FIG. 2B). Temporally, IL-6 mRNA and protein were sequentially up-regulated at the earliest time points following wounding, consistent with a role for this pathway in initiating WIHN (FIG. 2C).

Figure 2D:
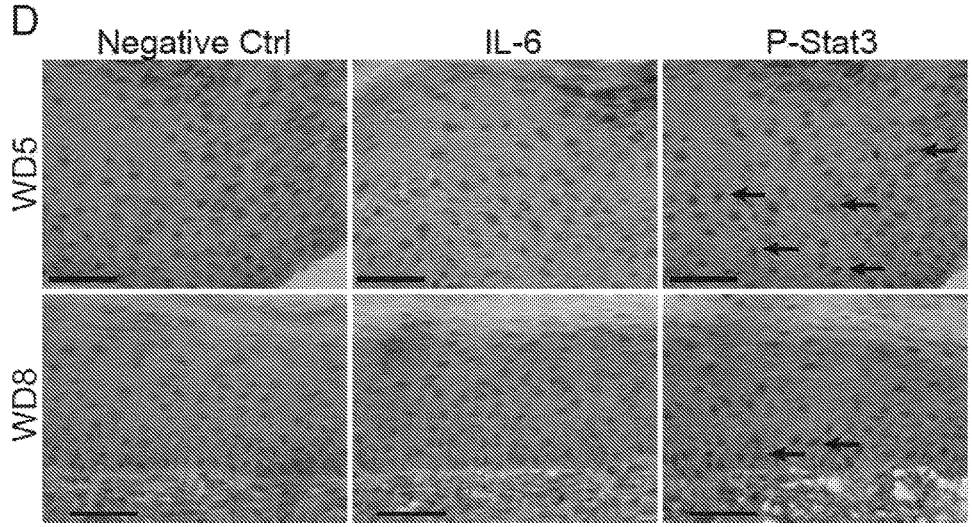
Figure 2E:
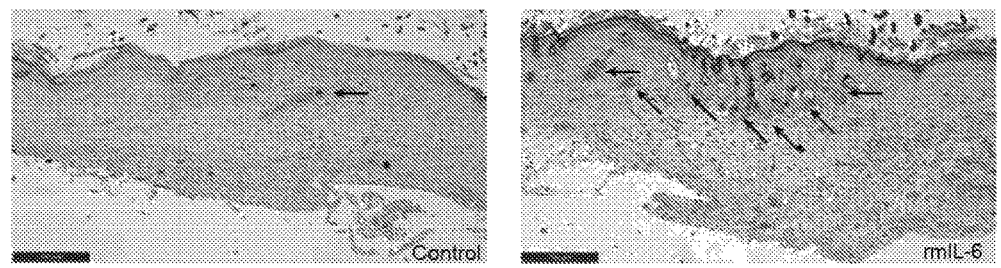
Figure 2F:
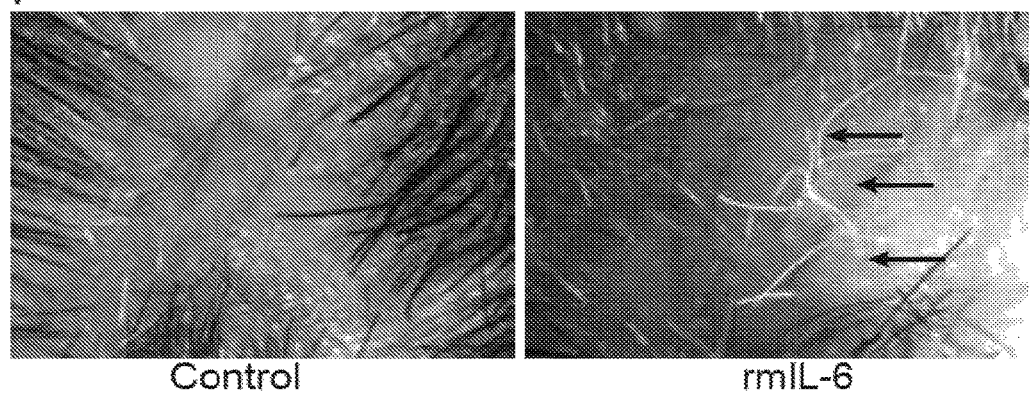
Figure 2G:
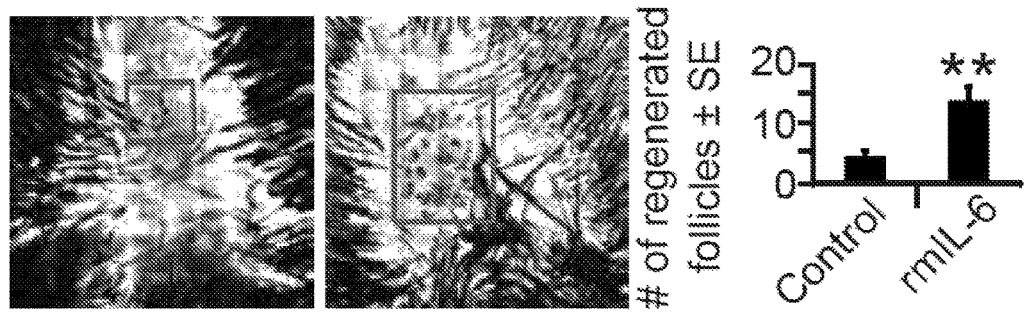
Figure 2H:
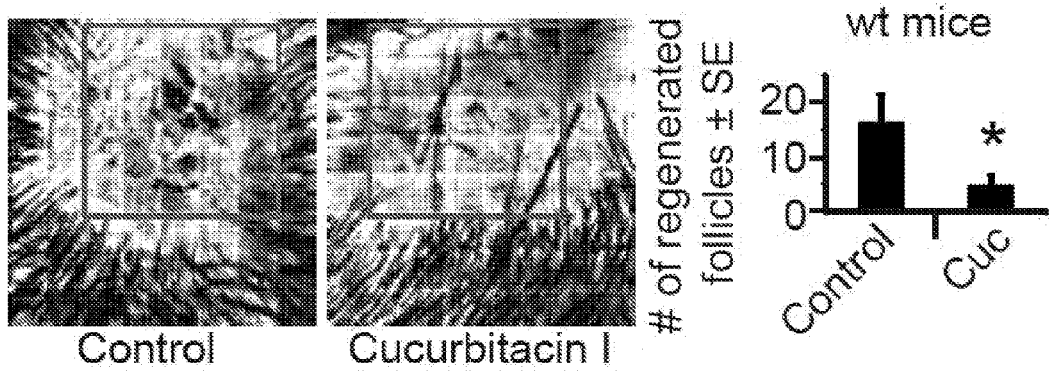
Figure 2I:
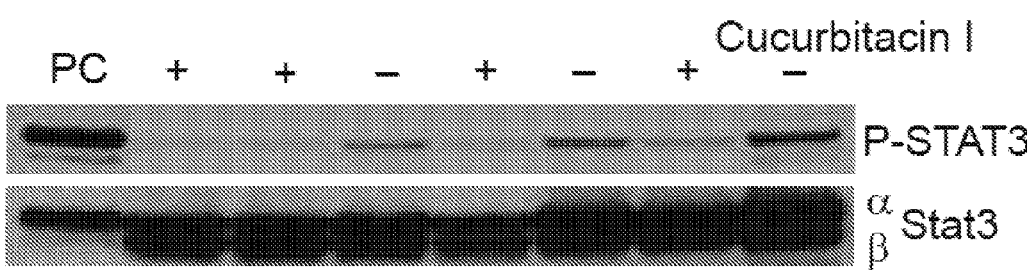

IL-6 receptor engagement is known to cause phosphorylation of STAT3, leading to its nuclear translocation and transcriptional activation (Heinrich et al., 2003). Consistent with a role for IL-6 signaling in WIHN initiation, we observed increased IL-6 and pSTAT3 protein in keratinocytes at PWD5 and 8 (FIG. 2D). To test the functional consequences of IL-6 in follicle regeneration, we injected recombinant IL-6 protein into mice following wounding and examined subsequent hair follicle regeneration. Compared to vehicle injected controls, mice receiving IL-6 had a nearly 3-fold increase in the number of regenerated follicles (FIG. 2 E-G). Conversely, mice injected with the IL-6/STAT3 pathway inhibitor cucurbitacin I had a greater than 3-fold decrease in the number of regenerated follicles (FIG. 2H). Cucurbitacin I strongly suppressed STAT3 phosphorylation in these mice (FIG. 2I), confirming inhibition of the IL-6 pathway. In aggregate, these data suggest that TLR3 activation during wounding leads to IL-6 production and STAT3 phosphorylation resulting in higher regeneration.

TLR3 Activation Induces Stem Cell Phenotypes in Keratinocytes. During physiologic skin renewal, keratinocyte differentiation proceeds in a highly ordered fashion known as stratification. Epithelial stem cells abutting the basement membrane divide and give rise to progressively more differentiated keratinocytes as they approach the skin surface and are ultimately sloughed (Fuchs and Raghavan, 2002). By contrast, physiologic hair cycling entails mobilization of distinct cells located in the hair follicle stem cell compartment in the bulge region (Millar, 2002). Previous studies revealed that keratinocytes outside of the bulge region— which ordinarily differentiate into corneocytes during stratification—contribute to regenerated hair follicles during WIHN (Ito et al., 2007). This finding implies that the normal stratification program is altered in skin regeneration. We hypothesized that TLR3 activation during WIHN may prevent normal stratification in keratinocytes and maintain them in a less differentiated, stem cell-like state.

Figure 3A:
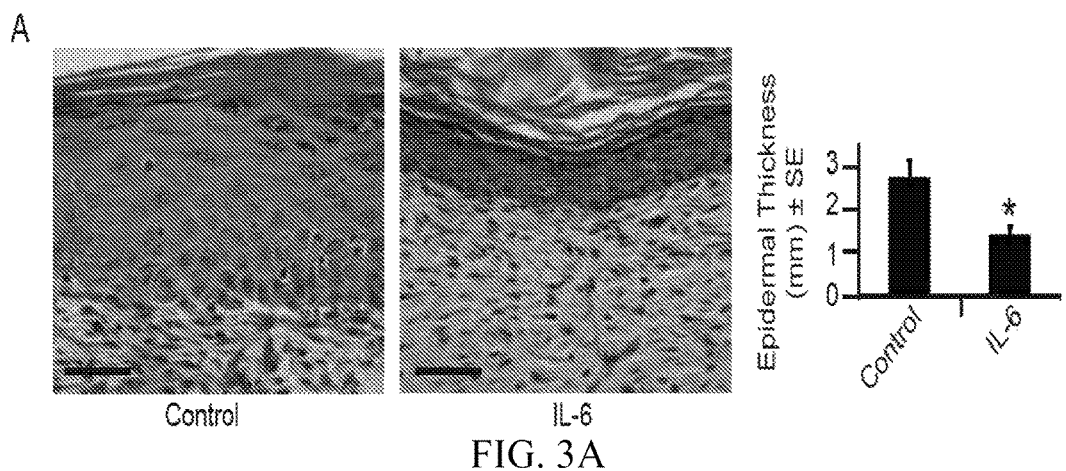
FIG. 3: TLR3 activation inhibits keratinocyte differentiation. A) Cross-sectional H&E histology through healed scars treated with IL-6 (25 ng) or control (PBS) at WD7. Scale bar=100 μm. Quantification of healed epidermal thickness in healed scars after control or IL-6 addition. B) Mean fold change in KRT1 mRNA after IL-6 (50 ng/mL)+/−cucurbitacin I in NHEK for 24 hours as determined by qRT-PCR and normalized to housekeeping gene, RPLP0. C) Mean fold change in KRT1 mRNA after poly (I:C) (20 μg/mL) addition to NHEK for 24 hours as determined by qRT-PCR and normalized as in 3B. D) Mean fold change in FLG mRNA after poly (I:C) given and normalized as in 3C. E) Mean fold change in KRT1 mRNA with TLR3-specific or scrambled control siRNA in the presence of poly (I:C) (20 μg/mL) in NHEK as determined by qRT-PCR and normalized as in 3B. F) Mean fold change in KRT1 mRNA with TLR3-specific inhibitor or control in the presence of poly (I:C) (20 μg/mL) in NHEK as determined by qRT-PCR and normalized as in 3B. *p<0.05 by Student's T-test or Single Factor ANOVA.
Figure 3B:
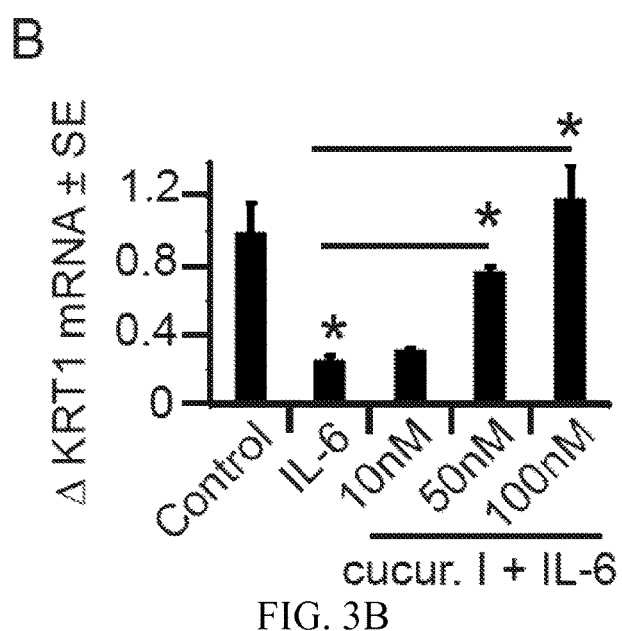
Figure 3C:
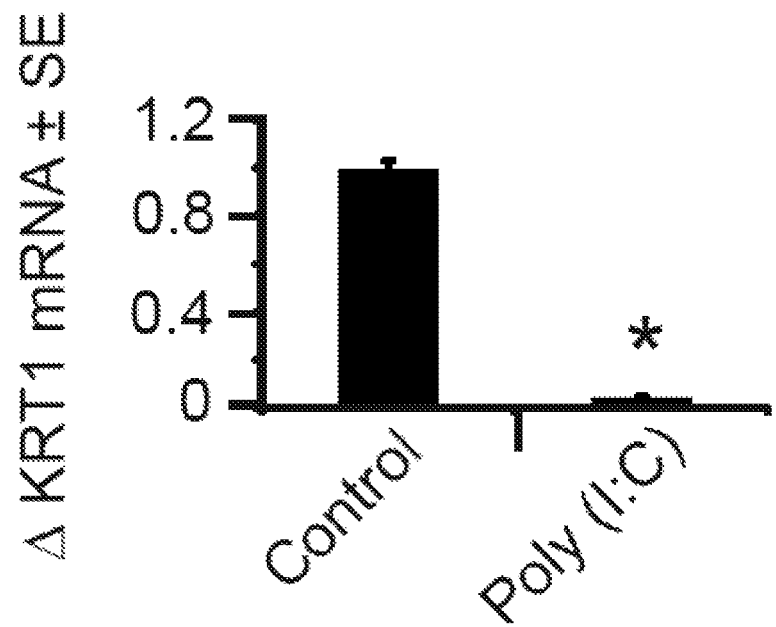
Figure 3D:
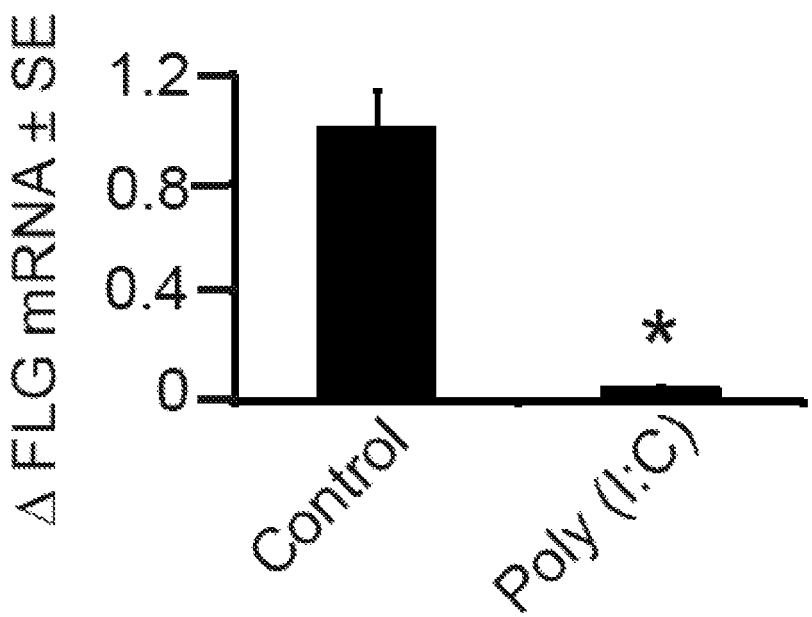
Figure 3E:
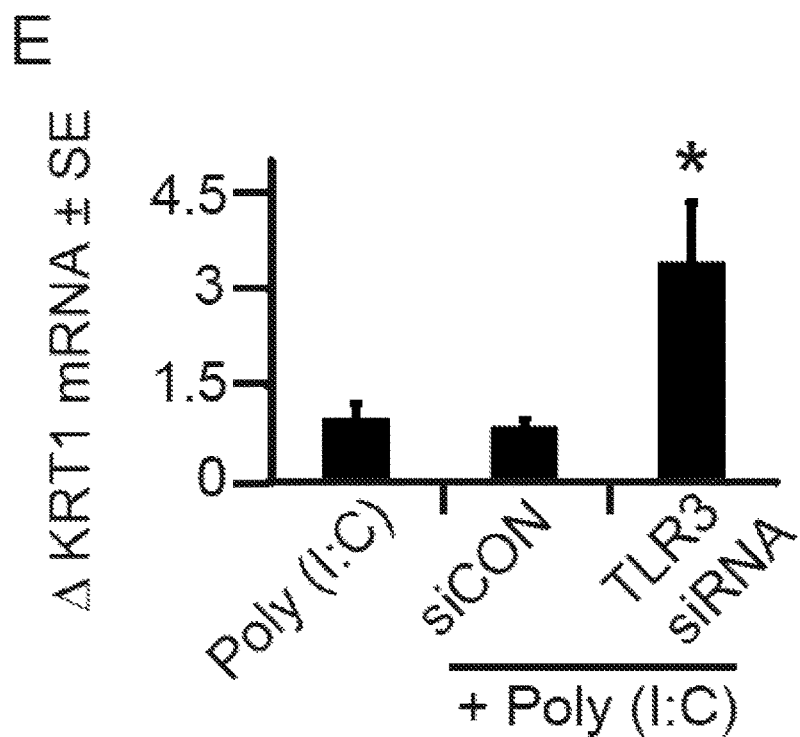
Figure 3F:
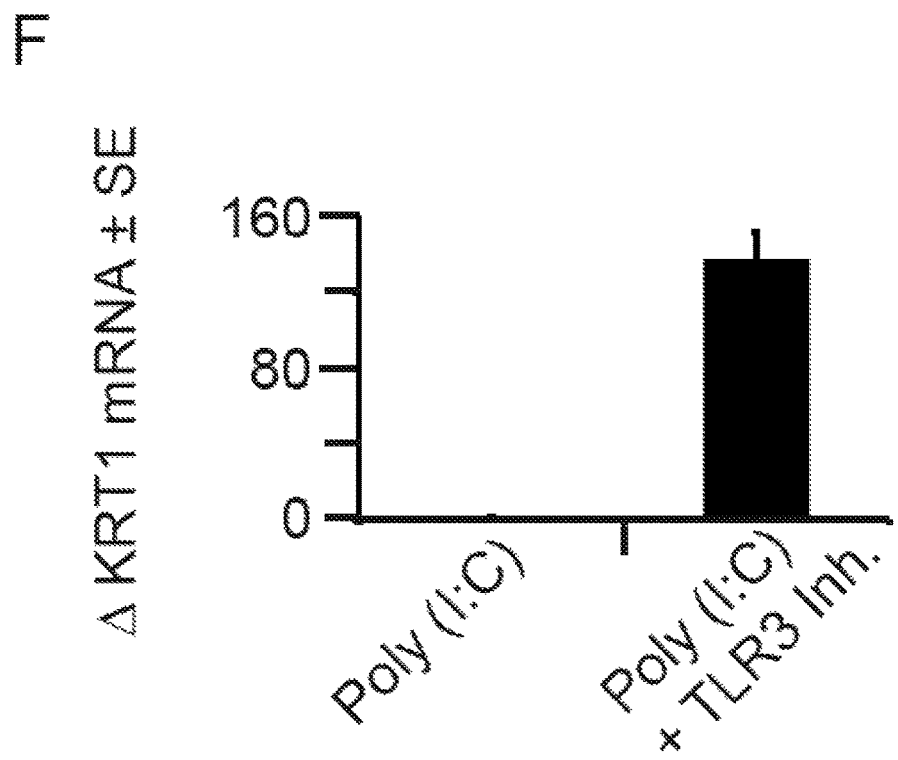
Figure 10A:
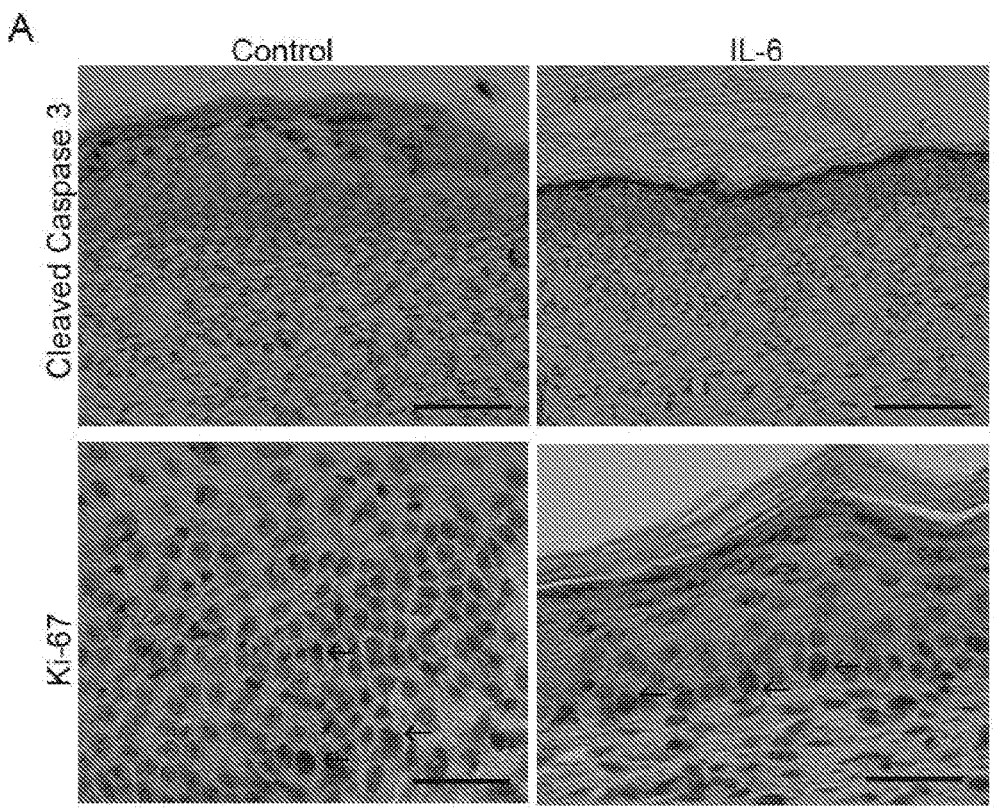
FIG. 10: Increased stratification after IL-6 and TLR3 activation in keratinocytes. A) Cleaved caspase 3 and Ki-67 immunohistochemistry on healed murine wounds after rmIL-6 treatment; representative images are shown. Scale bar=100 μm for cleaved Caspase 3, 50 μm for Ki-67; original magnification: 20×. B) Mean fold change in TLR3 mRNA with TLR3-specific siRNA or siCON (control siRNA) 24 hours after poly(I:C) treatment of NHEKs for 24 hours as determined by qRT-PCR and normalized to housekeeping gene, RPLP0. N=3, * p<0.05.
Figure 10B:
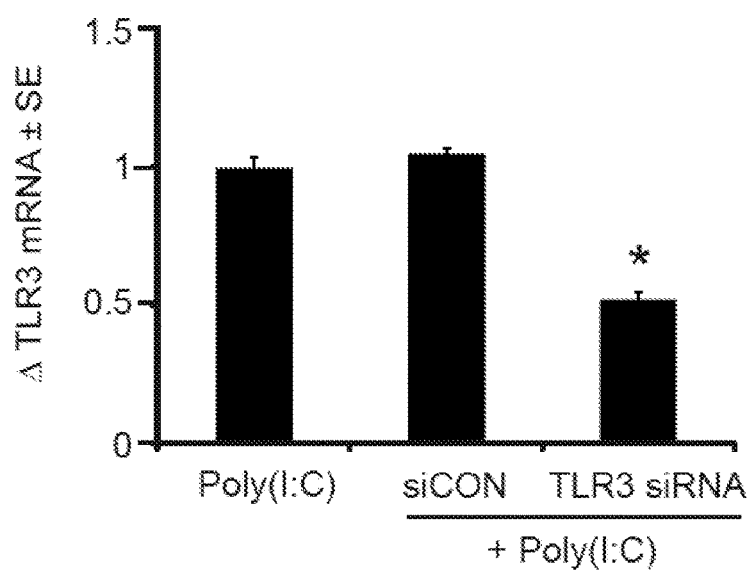

To test this idea, we first injected mice with IL-6 and assessed epidermal thickness as an index of stratification. Ordinarily, stratification causes thickening of the epidermis due to the accumulation of differentiated keratinocytes. However, mice treated with IL-6 had a 2-fold reduction in epidermal thickness compared to strain matched controls, implying decreased stratification (FIG. 3A) since no alterations in apoptosis or proliferation were observed with IL-6 treatment (FIG. 10A). Consistent with this, keratinocytes treated with IL-6 had a profound decrease in markers of keratinocyte differentiation, such as Keratin 1 (KRT1), an effect that was reversed by the addition of cucurbitacin I (FIG. 3B). Similarly, direct TLR3 activation with poly (I:C) in cultured keratinocytes led to a nearly complete loss of KRT1 and filaggrin (FLG) expression, another marker of keratinocyte differentiation. (FIG. 3C, D). This effect was TLR3-dependent as inhibition of TLR3 through siRNA mediated depletion or direct small molecule based antagonism abrogated the loss of KRT1 (FIG. 3E,F; FIG. 10B). These data suggest that induction of the TLR3/IL-6 axis during wounding prevents keratinocyte differentiation.

Figure 4A:
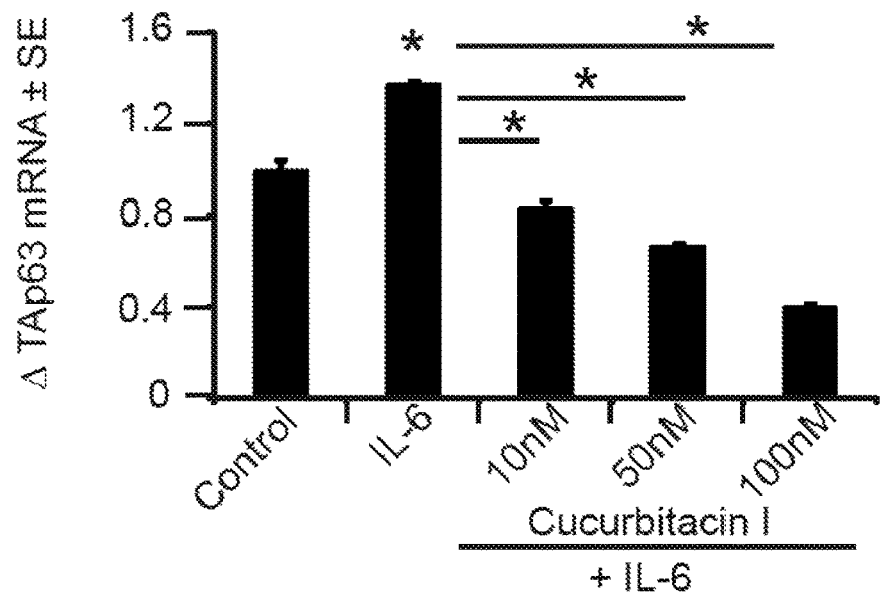
FIG. 4: dsRNA and IL-6 induce keratinocyte stem cell genes. A) Mean fold change in TAp63 mRNA after IL-6 protein (50 ng/mL)+/−cucurbitacin I in NHEK as determined by qRT-PCR and normalized to housekeeping gene, RPLP0. B) TAp63 protein levels after IL-6 (25 ng) compared to PBS control in wt mice measured by western blot; normalized to β-actin. C) TAp63 and ΔNp63 protein levels after cucurbitacin I (2 mg/kg) compared to PBS control in wt mice measured by western blot; normalized to β-actin. D) Mean fold change in KRT1 mRNA with TAp63-specific or scrambled control siRNA in the presence of IL-6 (50 ng/mL) in NHEK as determined by qRT-PCR and normalized to housekeeping gene, RPLP0. E) Mean fold change in CBX4 mRNA after poly (I:C) (20 μg/mL) addition to NHEK for 24 hours as determined by qRT-PCR and normalized as in 4D. F) Mean fold change in CBX4 mRNA after IL-6 (50 ng/mL)+/−cucurbitacin I in NHEK for 24 hours as determined by qRT-PCR and normalized as in 4D. G) Mean fold change in KRT15 mRNA 72 hours after 24 hours of poly (I:C) (20 μg/mL) treatment to NHEK as determined by qRT-PCR and normalized as in 4D. H) Flow cytometry analysis of KRT15 protein expression 72 hours after 24 hours of poly (I:C) (20 μg/mL) or control to NHEK. *p<0.05 by Student's T-test or Single Factor ANOVA.
Figure 4B:
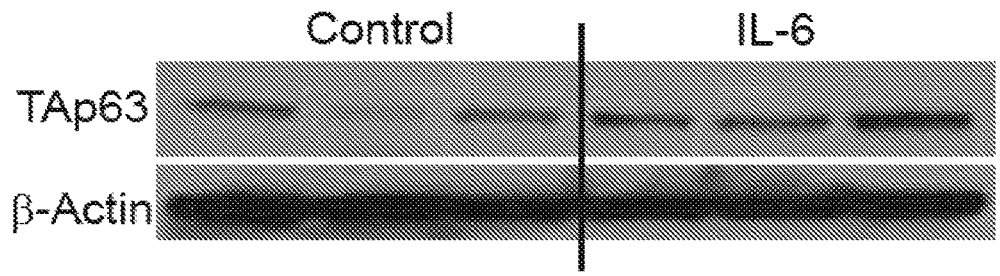
Figure 4B:
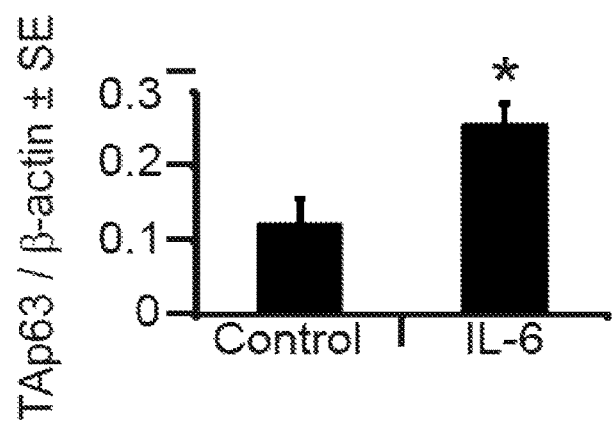
Figure 4C:
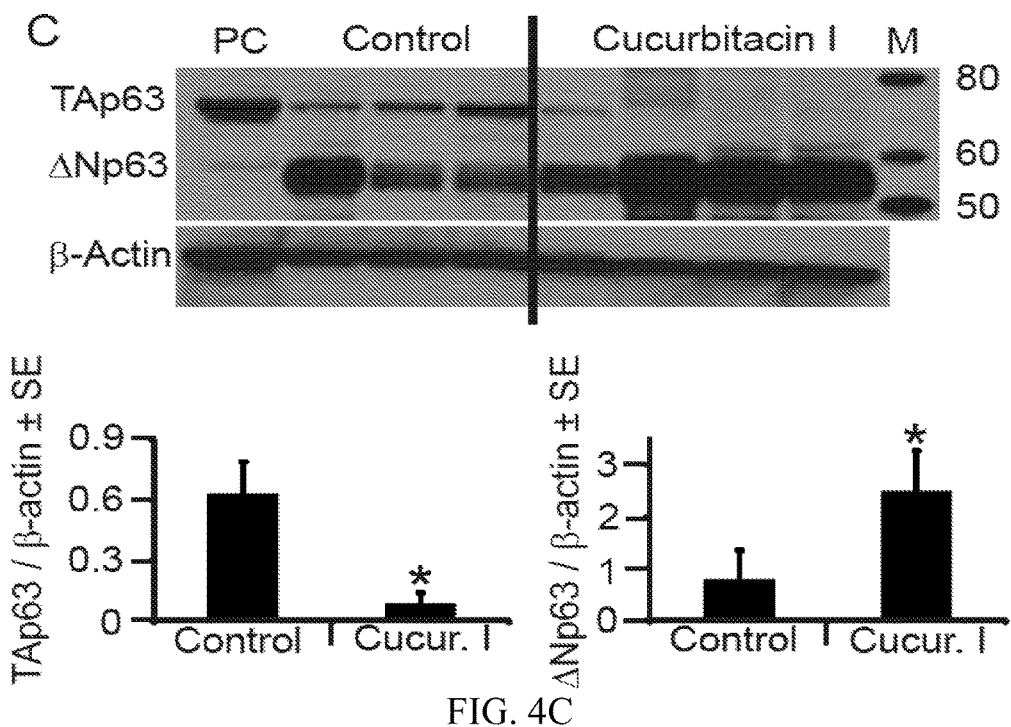
Figure 4D:
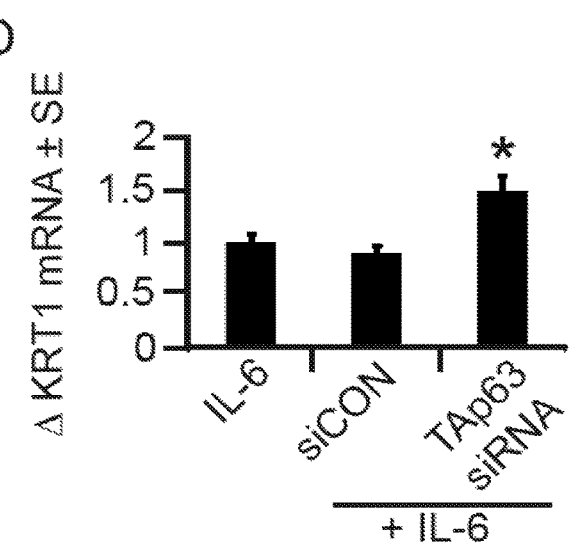
Figure 4E:
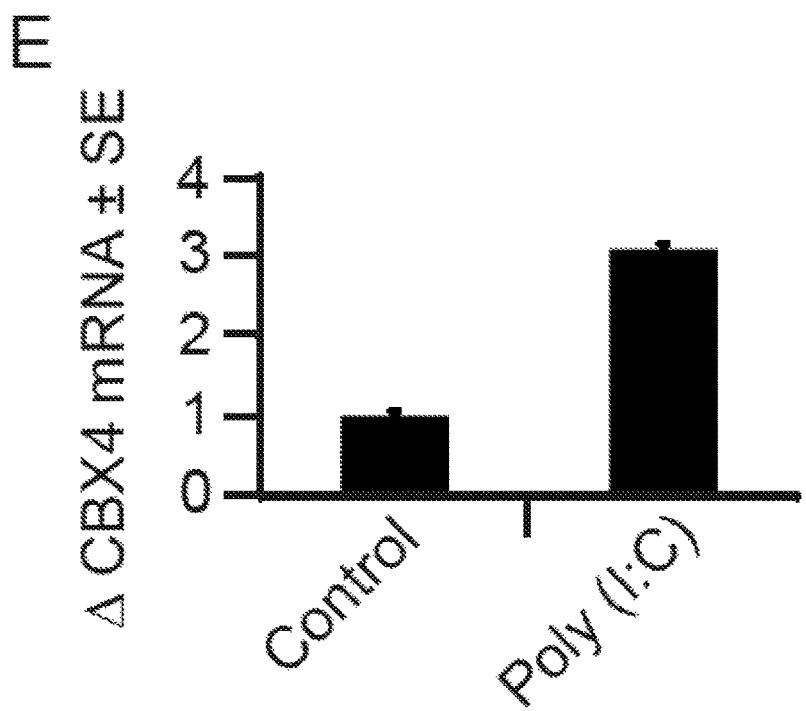
Figure 4F:
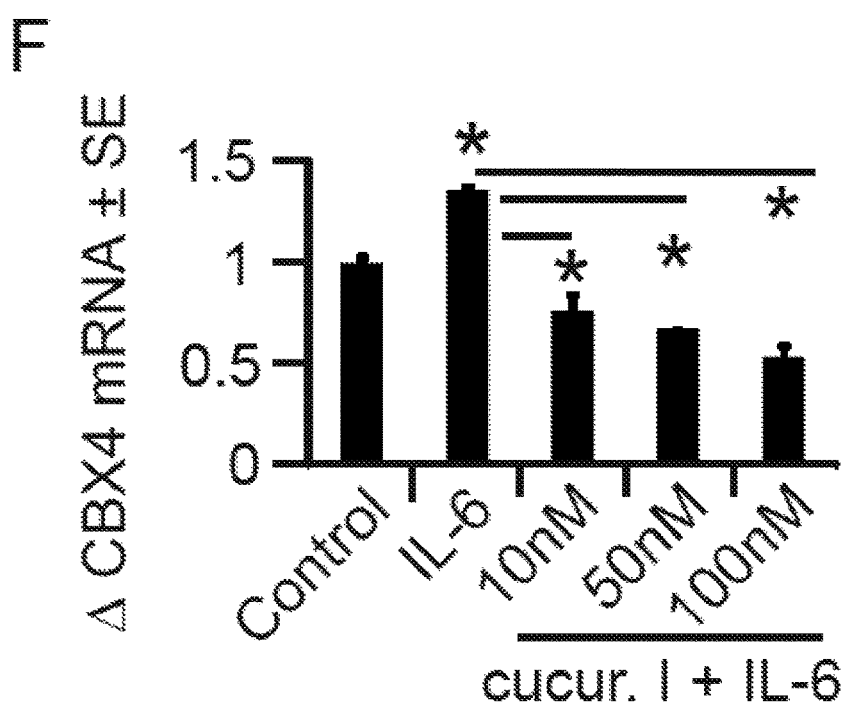
Figure 11A:
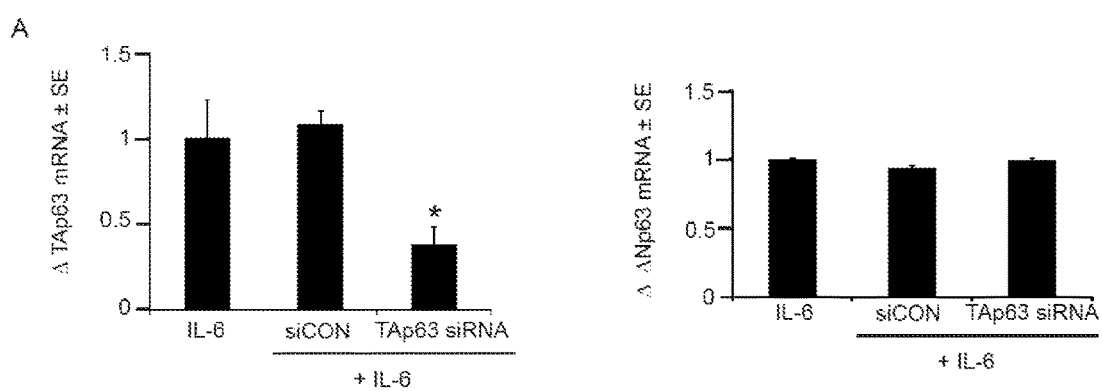
FIG. 11: TAp63-specific siRNA decreased expression of target gene by 50% or more in NHEK. A) Mean fold change in TAp63 and ΔNp63 mRNA with TAp63-specific siRNA or siCON (control siRNA) 24 hours after IL-6 treatment of NHEKs as determined by qRT-PCR and normalized to housekeeping gene, RPLP0. N=3, * p<0.05.

Epidermal stem cells express several transcriptional modulators required to maintain their undifferentiated and slow-cycling characteristics. Among the most important is TAp63, a transcription factor found in uncommitted surface ectoderm that modulates keratinocyte differentiation (Koster et al., 2004; Koster and Roop, 2004). We observed a modest increase TAp63 mRNA in cultured keratinocytes treated with IL-6, an effect that was reversed by cucurbitacin I (FIG. 4A). A similar effect was seen in mice treated with IL-6, with a 2.5 fold increase in the amount of TAp63 protein (FIG. 4B). Injection of mice with cucurbitacin I reversed this effect, with a decrease in TAp63 protein and a corresponding increase in ANp63, an alternative isoform of p63 induced in differentiating epidermis (FIG. 4C) (Koster et al., 2004). To examine whether TAp63 is required to prevent differentiation when the IL-6 pathway is activated, we depleted TAp63 in keratinocytes using siRNA. Indeed, upon addition of IL-6, TAp63-depleted keratinocytes had significantly higher KRT1 expression than did control cells (FIG. 4D, FIG. 11). Another transcriptional modulator up-regulated in epidermal stem cells is CBX4 (Luis et al., 2012b). This polycomb protein has been shown to bind to the promoters of several genes required for keratinocyte differentiation, resulting in transcriptional repression (Luis et al., 2012a; Luis et al., 2012b). We observed an increase in CBX4 expression upon activation of the TLR3 pathway with poly (I:C) or with addition of the downstream component IL-6. Again, this effect was reversed with addition of the IL-6 pathway inhibitor cucurbitacin I (FIG. 4E, F). The observed induction of TAp63 and CBX4 in these assays implies the activation of an epidermal stem cell program in keratinocytes.

Figure 4G:
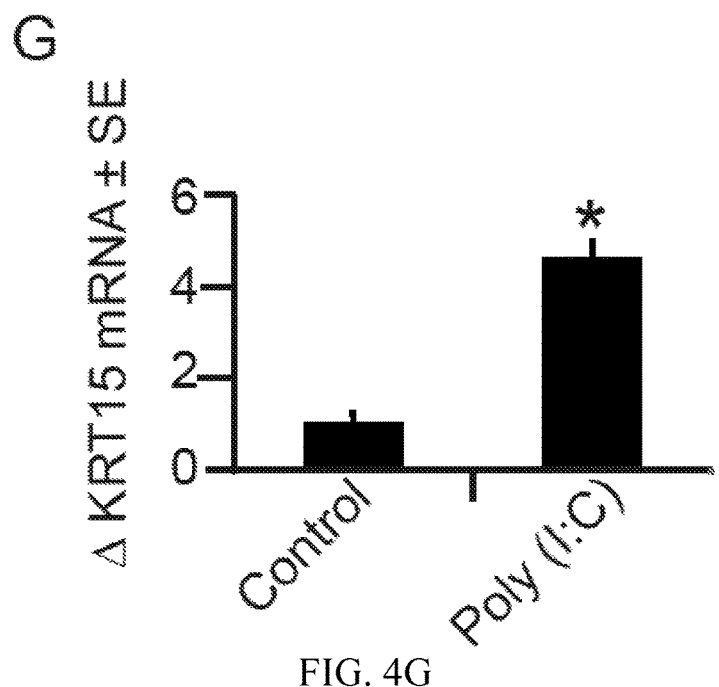
Figure 4H:
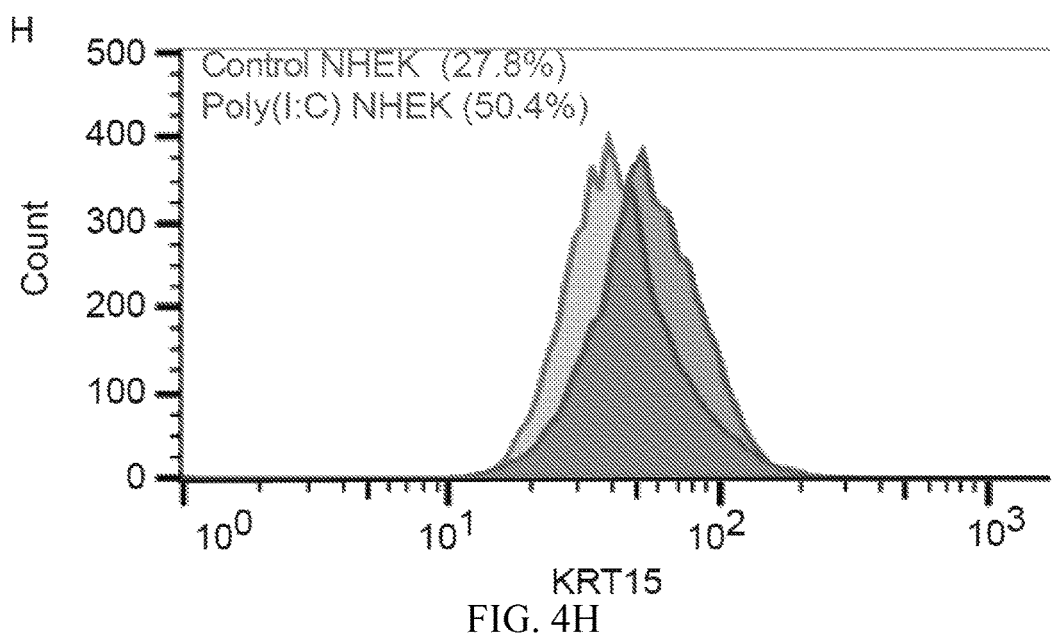

We sought more direct evidence that in response to TLR3 activation keratinocytes were adopting a stem cell phenotype permissive for subsequent hair follicle differentiation. Hair follicle stem cells residing in the bulge region of the follicle express keratin 15 (KRT15), which is considered the most reliable marker of this population (Liu et al., 2003). We found significantly increased expression of KRT15 mRNA in keratinocytes upon activation of TLR3 with poly (I:C) (FIG. 4G). Further, poly (I:C) addition nearly doubled the percentage of KRT15 expressing cells as assessed by FACS (FIG. 4H). Taken together, these data suggest that TLR3 pathway activation prevents keratinocyte differentiation and promotes acquisition of hair follicle stem cell attributes.

Figure 5A:
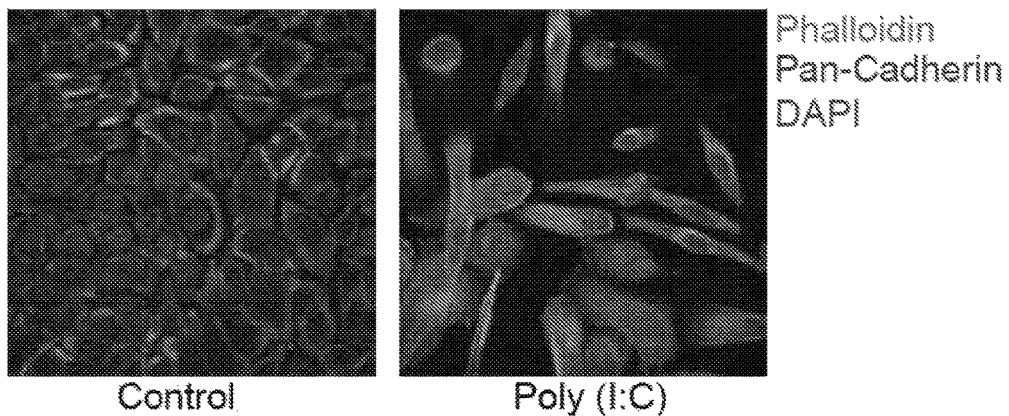
FIG. 5: TLR3 activation promotes keratinocyte hair follicle morphogenic program. A) Keratinocyte morphology 72 hours after 24 hours of poly (I:C) (20 μg/mL) or control treatment to NHEK as determined immunofluorescence staining with phalloidin (green), pancadherin (red) and DAPI (blue). Magnification=60x. B) Quantitation of length to width ratio of keratinocyte morphology as in 5A. C) Vimentin and keratin 5 immunofluorescence staining in NHEK after poly (I:C) or control as in 5A. D) Mean fold change in VIM mRNA after poly (I:C) (20 μg/mL) addition to NHEK for 24 hours at indicated time points as determined by qRT-PCR and normalized to housekeeping gene, RPLP0. E) Quantification of vimentin expression via flow cytometry in NHEK after poly (I:C) or control as in 5A or normal fibroblasts. F) β-catenin immunofluorescence staining in NHEK after poly (I:C) or control as in 5A. G) Quantitation of nuclear β-catenin to total levels of β-catenin in NHEK as in 5A. H) Mean fold change in LEF1, GLI1, SHH and EDAR mRNA after poly (I:C) treatment as in 5A addition determined by qRT-PCR and normalized to housekeeping gene, RPLP0 I) Mean fold change in LEF1 and SHH mRNA with TLR3-specific inhibitor or control in the presence of poly (I:C) in NHEK as determined by qRT-PCR as in 5H. J) Mean fold change in LEF1, GLI2, EDAR and SHH mRNA in TLR3KO mice compared to strain-matched control mice as determined by qRT-PCR. *p<0.05 by Student's T-test or Single Factor ANOVA.
Figure 5B:
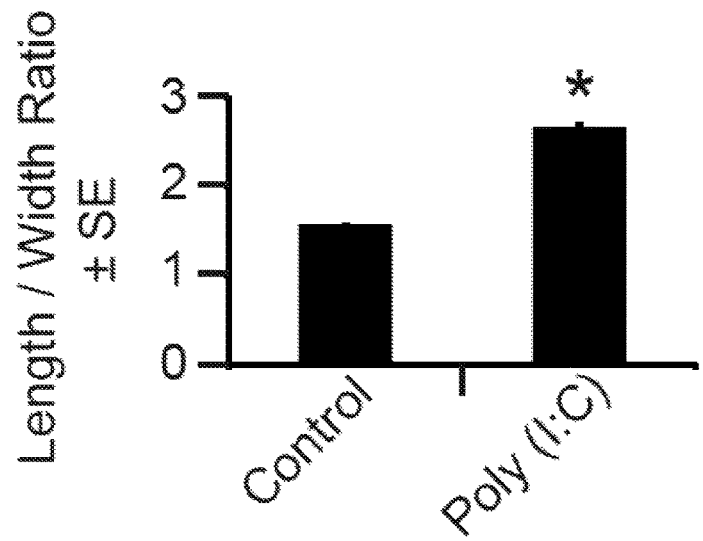
Figure 5C:
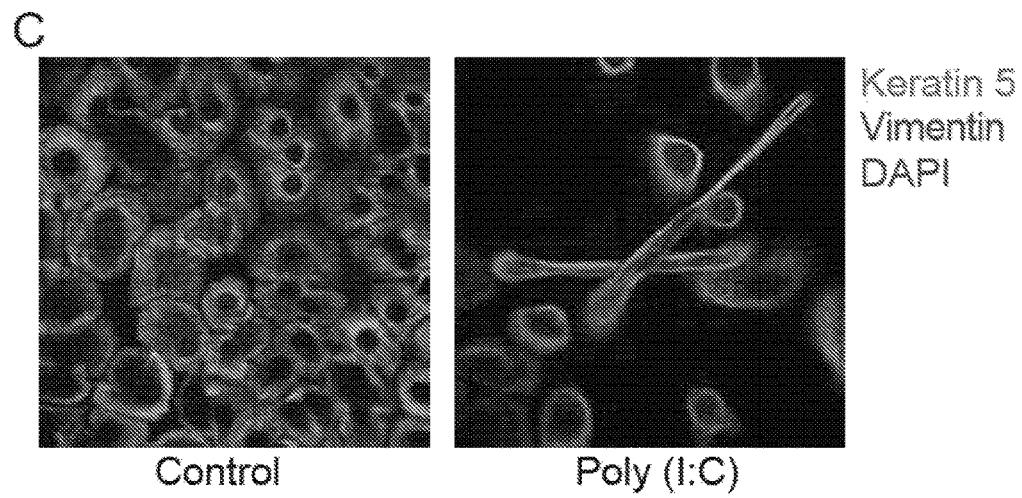
Figure 5D:
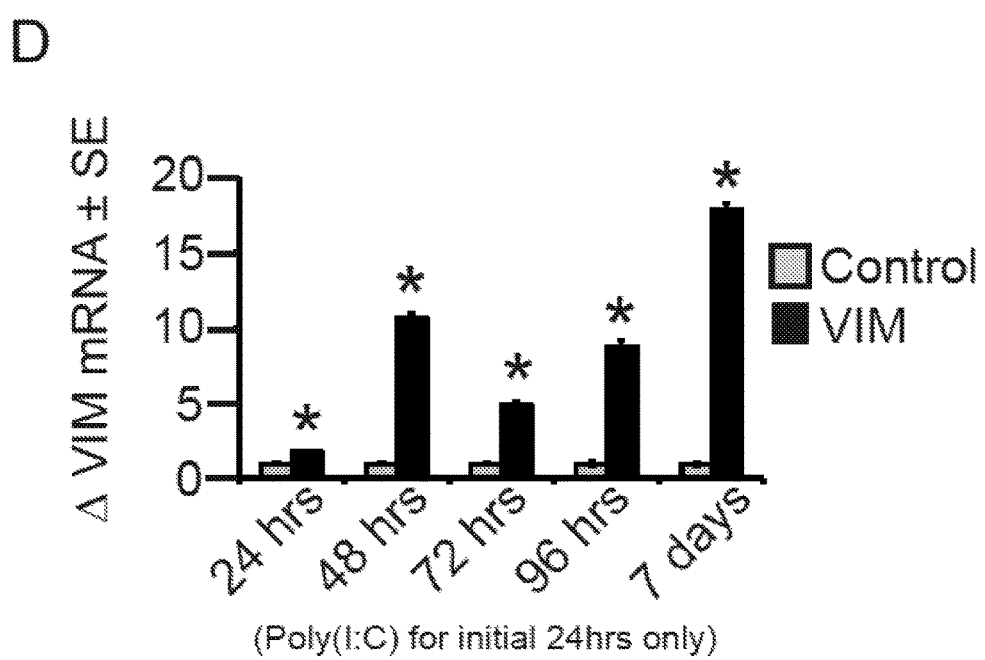
Figure 5E:
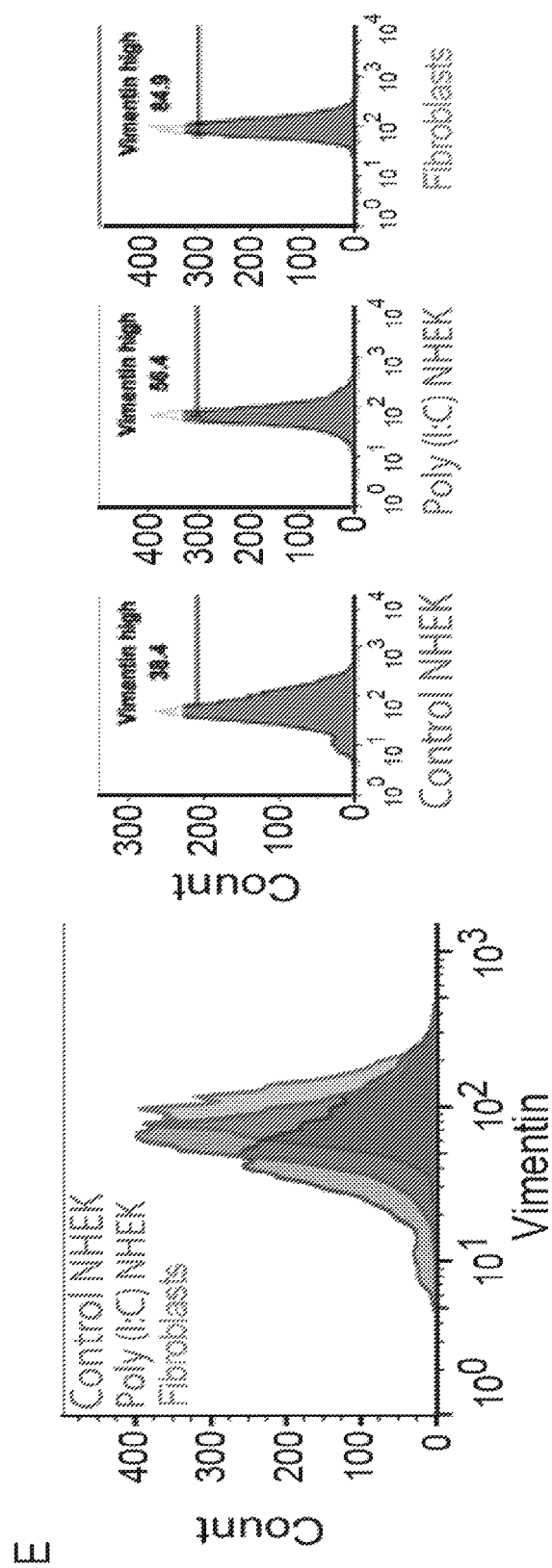

Hair follicle morphogenic pathways are induced by TLR3 signaling. The loss of differentiation and emergence of stem cell features we observed resembles the earliest events of epimorphic regeneration in the urodele limb (Mescher, 1996). After wounding, limb keratinocytes acquire a migratory phenotype and, along with underlying mesenchymal cells, become multipotent prior to differentiating into the varied cell types of the missing limb. We wondered whether a similar process of acquired multipotency and subsequent differentiation may underlie WIHN. We first examined the morphology of keratinocytes treated with poly (I:C). Upon addition of dsRNA, keratinocytes in culture lost their characteristic cuboidal appearance and assumed a long, spindle-like morphology more commonly observed in fibroblasts or in migratory keratinocytes during wound healing (FIG. 5A). Quantification of this morphologic change revealed a near doubling of the length-width ratio upon poly (I:C) addition (FIG. 5B). The fibroblast-like appearance of these cells prompted us to examine expression of vimentin, an intermediate filament gene expressed in fibroblasts and in cells undergoing epithelial to mesenchymal transitions (EMT) (FIG. 5C)(Lamouille et al., 2014). Following poly (I:C) administration for 24 hours, vimentin expression continued to increase in a time-dependent fashion (FIG. 5D). The epithelial marker E-cadherin was not reduced under these same conditions, however, distinguishing this phenomenon from full EMT. Consistent with this, vimentin protein expression in poly (I:C) treated cells was intermediate between that of control keratinocytes and fibroblasts (FIG. 5E). This partial activation of a mesenchymal phenotype is consistent with the activation of keratinocytes toward wound healing and has been observed in healing human skin wounds (Yan et al., 2010).

Figure 5F:
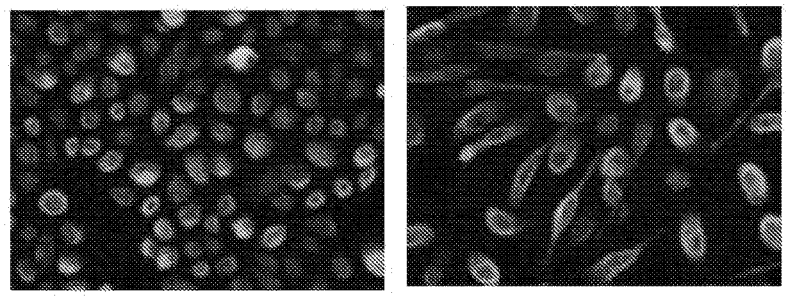
Figure 5G:
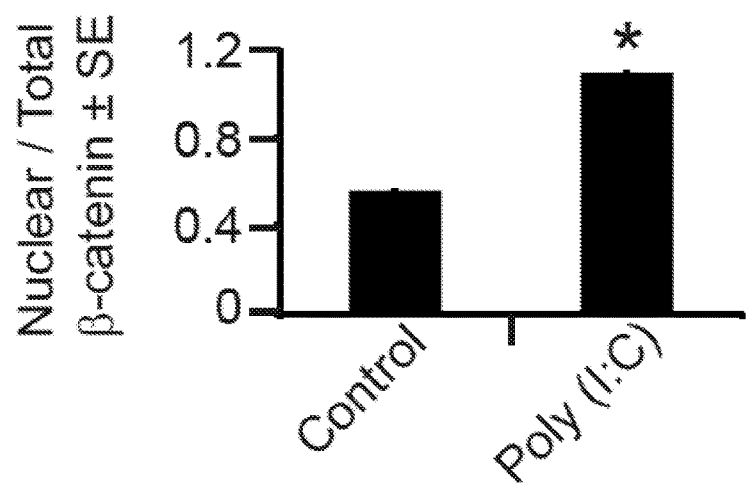
Figure 5H:
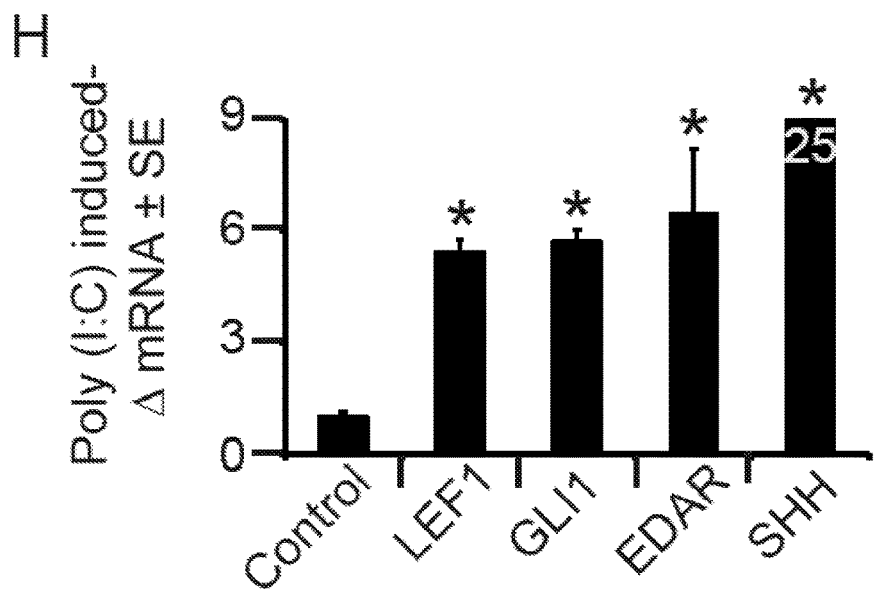
Figure 5I:
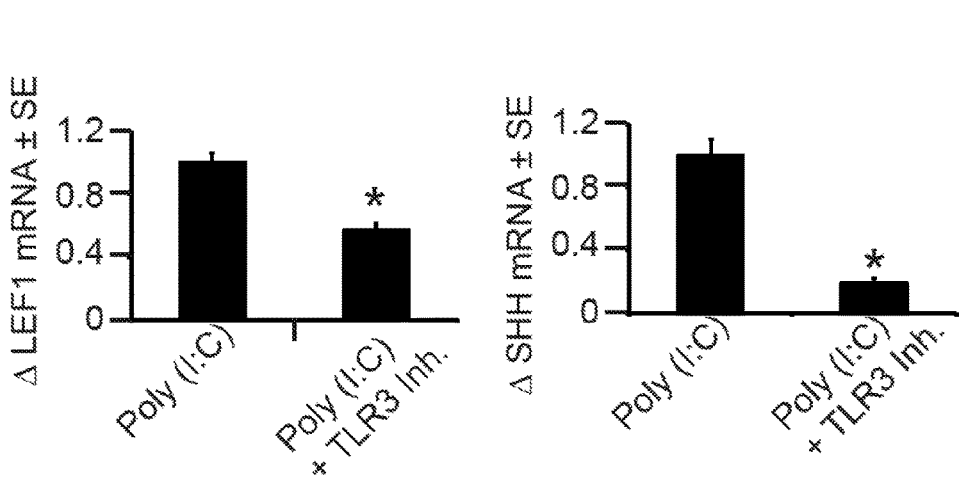
Figure 5J:
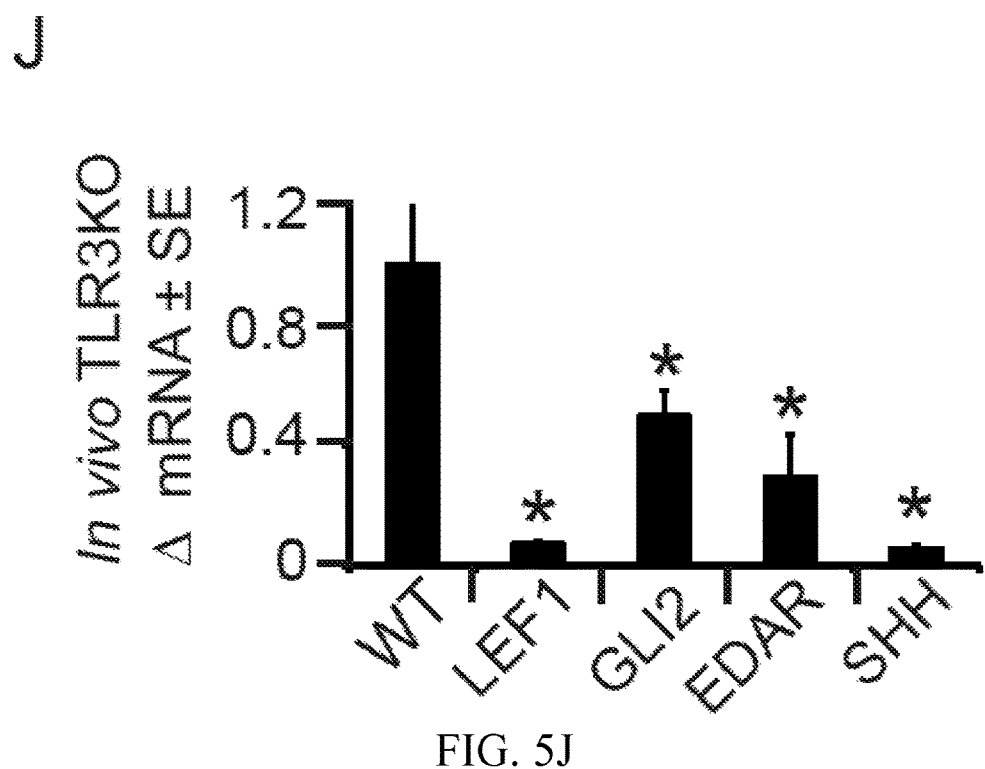

We wondered whether these poly (I:C) treated keratinocytes—with their altered morphology and with induction of epithelial stem cell genes—would be poised for subsequent activation of the hair follicle morphogenetic program. Core to this program are the Shh and Wnt pathways, which are activated during both embryonic hair follicle formation and in regeneration following wounding (Ito et al., 2007). We first examined β-catenin translocation to the nucleus, one of the earliest events in canonical Wnt signaling (Barker, 2008). TLR3 activation with poly (I:C) induced mostly a peri-nuclear accumulation, but also doubled the amount of nuclear β-catenin in keratinocytes, consistent with activation of the Wnt pathway (FIG. 5F-G). In addition, expression of the downstream Wnt effector and target LEF1 was up-regulated following poly (I:C) treatment of keratinocytes. Similarly, the expression of Shh pathway components SHH and GLI1 was increased following poly (I:C) addition, as was EDAR another gene active in skin appendage formation (FIG. 5H). These pathways were stably induced for several days despite a transient 24 hour treatment of keratinocytes with poly (I:C), suggesting that the keratinocytes may be primed toward a hair follicle or appendage fate. This pathway activation is TLR3-dependent as pretreatment of cells with a specific TLR3 small molecule antagonist markedly reduced the expression of both LEF1 and SHH (FIG. 5I) and in healed wounds, TLR3 KO mice have decreased expression of LEF1,GLI2, SHH and EDAR, compared to strain-matched control (FIG. 5J).

Figure 6A:
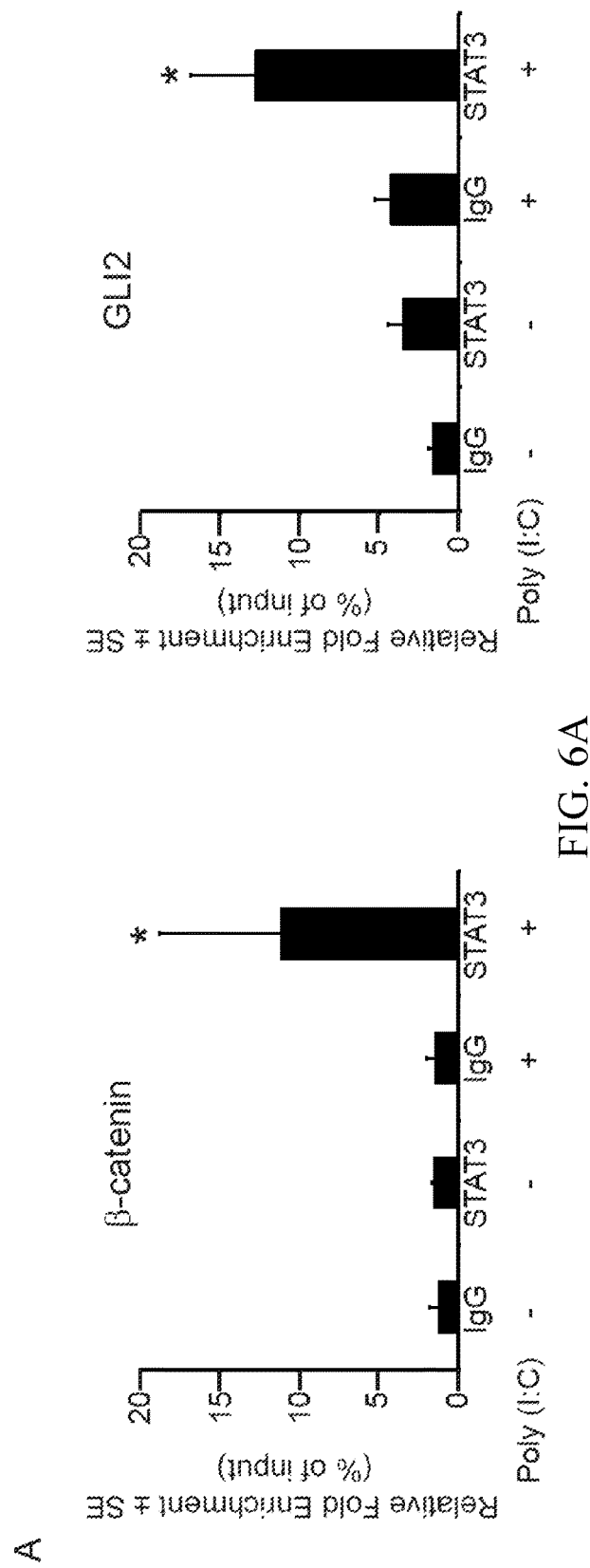
FIG. 6: TLR3 activation increases STAT3 occupancy of β-catenin and GLI2 promoters. A) Relative fold enrichment of STAT3 occupation at β-catenin and GLI2 promoter sites after poly (I:C) treatment of keratinocytes. N=5, p<0.05.

Having confirmed a phenotypic and molecular connection between the TLR3 pathway with regeneration and morphogenesis pathways respectively, we next sought to identify a direct mechanistic link. Since our data demonstrated that TLR3 activation leads to STAT3 activation, we investigated whether STAT3 binding sites are present in the promoters of the transcription factors for the wnt and shh pathways. Indeed, using ChIP-qPCR, we observed a significant increase in STAT3 occupation of both the β-catenin and GLI2 promoters upon poly (I:C) treatment in keratinocytes (FIG. 6). This data serves to demonstrate a direct link between dsRNA and activation of morphogenesis pathways.

Discussion dsRNAs are damage-associated signals that promote regeneration. While a capacity for regeneration is observed in representatives of almost all animal phyla, its distribution is far from uniform, with some species demonstrating regeneration of multiple body parts while closely related species fail to do so (Brockes et al., 2001). Urodele salamanders, for example, are well known to regenerate their limbs, yet among 24 urodele species examined, 4 failed to reconstitute limbs after amputation (Brockes et al., 2001). Even within a single species, differences in genetic background can lead to marked differences in regenerative ability. We found that the capacity to regenerate skin and hair follicles, a process termed wound induced hair neogenesis (WIHN), varies greatly among different strains of *mus musculus* (FIG. 1) (Nelson et al., 2013). We harnessed this variation and examined early time points following tissue damage, to search for initial, pivotal events that link wound healing to the reactivation of developmental programs.

For regeneration to occur, three interrelated events must take place: (1) organisms must sense loss of tissue integrity, (2) precursor cells must be mobilized to reconstitute missing structures, and (3) these cells must be directed along appropriate morphogenic pathways (Brockes et al., 2001). While the latter two processes have been extensively examined in studies of regeneration, less is known about how organisms sense damage and transduce this information to trigger a regenerative response. In hydra, the peptide head activator (HA) is secreted at sites of tissue damage and is required for regeneration (Sanchez Alvarado, 2006). In salamanders and newts, an unidentified, thrombin-activated serum factor initiates regeneration of both the limb and lens (Brockes et al., 2001; Imokawa and Brockes, 2003). No such triggers had been discovered in the rare examples of mammalian epimorphic regeneration.

Figure 7:
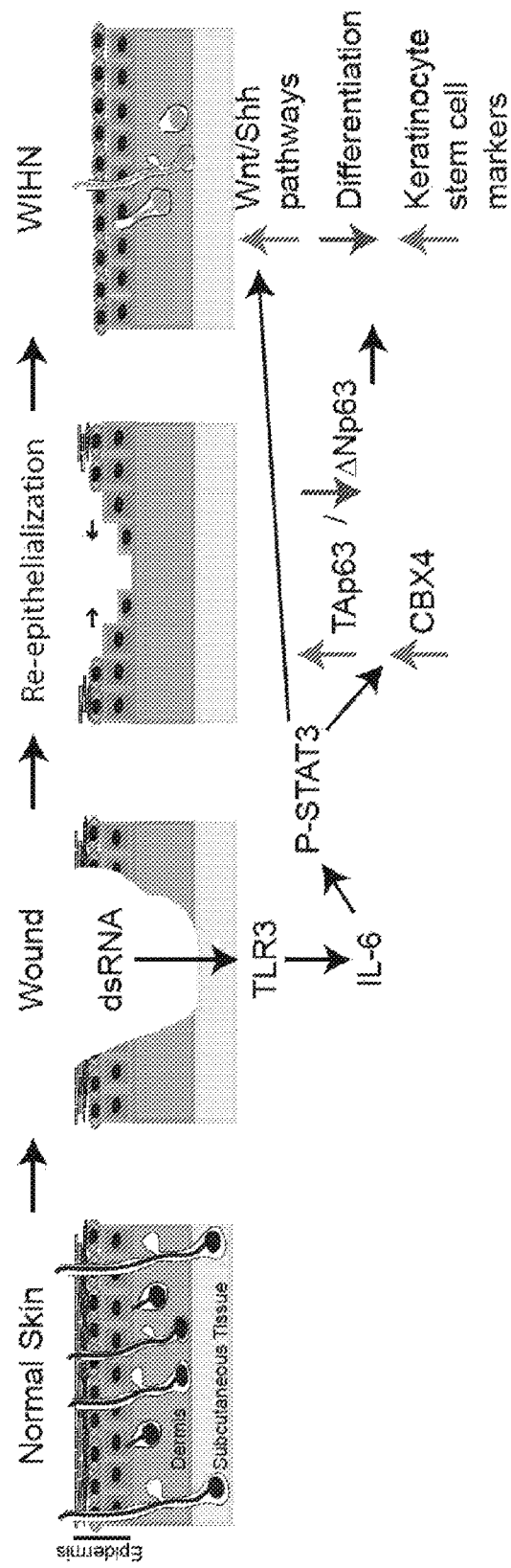
FIG. 7: Model representation of the proposed function of dsRNA/TLR3 and IL-6/STAT3 in the promotion of WIHN. Cutaneous wounding liberates dsRNA which binds to and activates TLR3 in keratinocytes. Downstream components of the TLR3 signal transduction cascade including IL-6 and pSTAT3 are induced. Activation of the TLR3/IL-6 axis leads to altered keratinocyte morphology and increased migration to form a wound epidermis. Keratinocytes of the wound epidermis exhibit stem cell features including expression of TAp63, CBX4, and KRT15. Subsequent activation of the Wnt, Shh pathways and EDAR leads to hair follicle morphogenesis.

In the context of WIHN, we identified dsRNA released by damaged cells as early molecular signals triggering regeneration (FIG. 7). Several lines of evidence support this: dsRNA responsive pathways are up-regulated in mice with a high capacity for regeneration, addition of exogenous dsRNA increases the number of regenerated follicles, and degradation of endogenous dsRNA inhibits regeneration (FIG. 1). Our results demonstrate that dsRNA initiates key events in the regeneration process following re-epithelialization.

Figure 12:
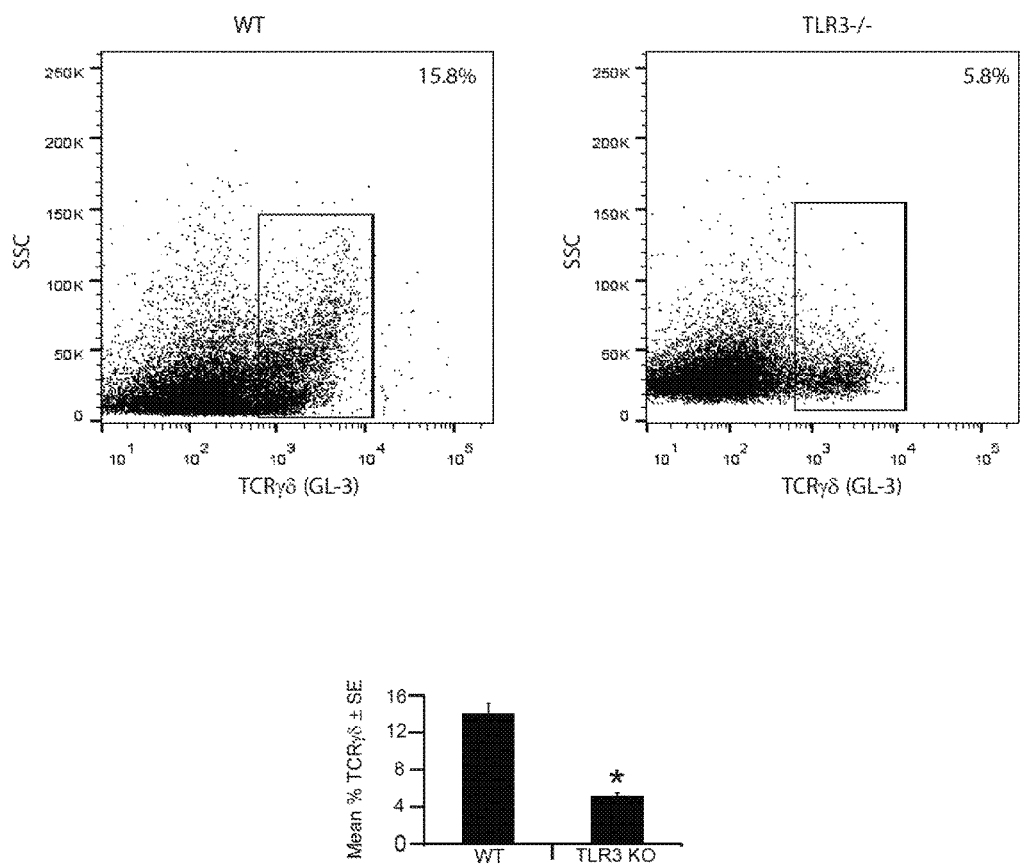
FIG. 12: TLR3 KO mice have fewer γβT-cells. Mean percentage of TCRγβ cells in newly reepithelialized wounds in wild type and TLR3 KO mice. Representative FlowJo dot plots are shown. N=3-5 mice per genotype; *p=0.001.

A major receptor for dsRNA in mammalian cells isTLR3. While originally identified for its role in response to viral pathogens, recent evidence has emerged that TLR3 plays a role in cutaneous wound healing. TLR3 is expressed in keratinocytes and TLR3 ligands stimulate keratinocyte proliferation in vitro and in vivo. Further, TLR3-defeicient animals have a decreased inflammatory response to wounding (Lai et al., 2009; Lebre et al., 2007). TLR3 is activated by mRNAs released from dying cells, linking its activation to tissue damage (Kariko et al., 2004). We find that TLR3 is activated in response to cutaneous wounding in mice as TLR3 mRNA is strongly induced, an effect that can be augmented by administration of exogenous dsRNA. The early and strong induction of TLR3 upon wounding coupled with the role of dsRNA in stimulating hair follicle neogenesis that we observed, suggest that TLR3 may relay information about tissue damage to activate regeneration. Of note, healed wounds of TLR3 KO mice also have significantly fewer γβ T-cells than wildtype mice (FIG. 12), which have been demonstrated as a necessary for WIHN (Gay et al., 2013). Intriguingly, downstream signaling pathways induced by TLR3—including now γβ T-cells—appear to differ among humans and mice (Lundberg et al., 2007). It will be interesting to examine whether differences in TLR3 responses account for the greater regeneration of skin wounds in mice compared to humans.

TLR3 activation increases keratinocyte stem cell markers. During both physiologic hair cycling, KRT15 expressing stem cells of the bulge are mobilized and differentiate into multiple subtypes of hair lineages. However, during WIHN cells of the interfollicular epidermis also contribute to regenerated hairs (Ito et al., 2007). We find an increase in markers of both types of keratinocyte stem cells upon activation of the TLR3 pathway. In keratinocytes isolated form interfollicular skin, we observed induction of KRT15 upon TLR3 pathway activation with dsRNA. Moreover, dsRNA addition induces keratinocytes to express transcriptional modulators associated with interfollicular keratinocyte stem cells including TAp63 and CBX4. Interestingly, TLR3 has been implicated in the reprogramming of fibroblasts to IPS cells using virally-encoded reprogramming factors (Lee et al., 2012). Activation of TLR3 by dsRNA during wounding may similarly convert keratinocytes destined to form stratified epidermis into cells with increased capacity for hair morphogenesis.

TLR3 activation initiates hair morphogenesis. The final event in regeneration is the reactivation of embryonic morphogenic programs to direct mobilized stem cells to form missing structures. Hair follicle morphogenesis in the developing embryo proceeds through epithelial-mesenchymal crosstalk between the undifferentiated epithelium and the underlying dermis. Our data provide the first physiologic role for TLR3 in Wnt and Shh pathway activation during regeneration, likely through promoting this crosstalk. As with Wnt and Shh signaling, we find EDAR pathway components are also activated in response to TLR3 signaling in vitro and in vivo. Activation of these appendage specification signals by dsRNA is TLR3 dependent since TLR3 chemical inhibition in vitro or TLR3 gene deletion in vivo blunt the Wnt and Shh pathway. Finally, STAT3 directly links TLR3 and these pathways since dsRNA increases occupancy at the promoters of β-Catenin and Gli2. Given the importance in hair development of in vivo epithelial-mesenchymal crosstalk to amplify EDAR, Wnt and Shh signaling (Millar, 2002) it is notable that we can detect induction of these pathways with keratinocytes alone. We hypothesize these signals will be enhanced in the presence of competent fibroblasts. These findings for TLR3 initiating morphogenesis are consistent with the original description of Toll receptors as regulators of dorsal ventral patterning in drosophila (Anderson et al., 1985); together with our findings, this suggests that Toll receptors have an equally important role in tissue specification in addition to their more well-known roles in innate immune activation.

In summary we identified the activation of TLR3 by damage induced dsRNA as the linchipin of the regenerative response to murine skin wounds. Strikingly, TLR3 plays a role in all three aspects of regeneration-damage sensing, stem cell recruitment, and activation of morphogenesis. As such, TLR3 agonists may be powerful therapeutics to decrease fibrosis and promote cutaneous regeneration.

REFERENCES

1. Anderson, K. V., Bokla, L., and Nusslein-Volhard, C. (1985). Establishment of dorsal-ventral polarity in the *Drosophila* embryo: the induction of polarity by the Toll gene product. Cell 42, 791-798.

2. Barker, N. (2008). The canonical Wnt/beta-catenin signalling pathway. Methods Mol Biol 468, 5-15.

3. Bernard, J. J., Cowing-Zitron, C., Nakatsuji, T., Muehleisen, B., Muto, J., Borkowski, A. W., Martinez, L., Greidinger, E. L., Yu, B. D., and Gallo, R. L. (2012). Ultraviolet radiation damages self non-coding RNA and is detected by TLR3. Nat Med.

4. Breedis, C. (1954). Regeneration of hair follicles and sebaceous glands from the epithelium of scars in the rabbit. Cancer Res 14, 575-579.

5. Brockes, J. P., Kumar, A., and Velloso, C. P. (2001). Regeneration as an evolutionary variable. Journal of anatomy 199, 3-11.

6. Carpenter, A. E., Jones, T. R., Lamprecht, M. R., Clarke, C., Kang, I. H., Friman, O., Guertin, D. A., Chang, J. H., Lindquist, R. A., Moffat, J., et al. (2006). CellProfiler: image analysis software for identifying and quantifying cell phenotypes. Genome biology 7, R100.

7. Fan, C., Luedtke, M. A., Prouty, S. M., Burrows, M., Kollias, N., and Cotsarelis, G. (2011). Characterization and quantification of wound-induced hair follicle neogenesis using in vivo confocal scanning laser microscopy. Skin Res Technol 17, 387-397.

8. Fuchs, E., and Raghavan, S. (2002). Getting under the skin of epidermal morphogenesis. Nat Rev Genet 3, 199-209.

9. Galun, E., and Rose-John, S. (2013). The regenerative activity of interleukin-6. Methods Mol Biol 982, 59-77.

10. Gay, D., Kwon, O., Zhang, Z., Spata, M., Plikus, M. V., Holler, P. D., Ito, M., Yang, Z., Treffeisen, E., Kim, C. D., et al. (2013). Fgf9 from dermal gammadelta T cells induces hair follicle neogenesis after wounding. Nat Med 19, 916-923.

11. Heinrich, P. C., Behrmann, I., Haan, S., Hermanns, H. M., Muller-Newen, G., and Schaper, F. (2003). Principles of interleukin (IL)-6-type cytokine signalling and its regulation. Biochem J 374, 1-20.

12. Imokawa, Y., and Brockes, J. P. (2003). Selective activation of thrombin is a critical determinant for vertebrate lens regeneration. Current biology: C B 13, 877-881.

13. Irizarry, R. A., Bolstad, B. M., Collin, F., Cope, L. M., Hobbs, B., and Speed, T. P. (2003). Summaries of Affymetrix GeneChip probe level data. Nucleic Acids Res 31, e15.

14. Ito, M., Yang, Z., Andl, T., Cui, C., Kim, N., Millar, S. E., and Cotsarelis, G. (2007). Wntdependent de novo hair follicle regeneration in adult mouse skin after wounding. Nature 447, 316-320.

15. Jia, C. (2011). Advances in the regulation of liver regeneration. Expert Rev Gastroenterol Hepatol 5, 105-121.

16. Kariko, K., Ni, H., Capodici, J., Lamphier, M., and Weissman, D. (2004). mRNA is an endogenous ligand for Toll-like receptor 3. J Biol Chem 279, 12542-12550.

17. Karim, R., Meyers, C., Backendorf, C., Ludigs, K., Offringa, R., van Ommen, G. J., Melief, C. J., van der Burg, S. H., and Boer, J. M. (2011). Human papillomavirus deregulates the response of a cellular network comprising of chemotactic and proinflammatory genes. PLoS One 6, e17848.

18. Kligman, A. M., and Strauss, J. S. (1956). The formation of vellus hair follicles from human adult epidermis. J Invest Dermatol 27, 19-23.

19. Koster, M. I., Kim, S., Mills, A. A., DeMayo, F. J., and Roop, D. R. (2004). p63 is the molecular switch for initiation of an epithelial stratification program. Genes Dev 18, 126-131.

20. Koster, M. I., and Roop, D. R. (2004). The role of p63 in development and differentiation of the epidermis. Journal of dermatological science 34, 3-9.

21. Lai, Y., Di Nardo, A., Nakatsuji, T., Leichtle, A., Yang, Y., Cogen, A. L., Wu, Z. R., Hooper, L. V., Schmidt, R. R., von Aulock, S., et al. (2009). Commensal bacteria regulate Toll-like receptor 3-dependent inflammation after skin injury. Nat Med 15, 1377-1382.

22. Lamouille, S., Xu, J., and Derynck, R. (2014). Molecular mechanisms of epithelial-mesenchymal transition. Nature reviews Molecular cell biology 15, 178-196.

23. Lebre, M. C., van der Aar, A. M., van Baarsen, L., van Capel, T. M., Schuitemaker, J. H., Kapsenberg, M. L., and de Jong, E. C. (2007). Human keratinocytes express functional Toll-like receptor 3, 4, 5, and 9. J Invest Dermatol 127, 331-341.

24. Lee, J., Sayed, N., Hunter, A., Au, K. F., Wong, W. H., Mocarski, E. S., Pera, R. R., Yakubov, E., and Cooke, J. P. (2012). Activation of innate immunity is required for efficient nuclear reprogramming. Cell 151, 547-558.

25. Lin, Q., Wang, L., Lin, Y., Liu, X., Ren, X., Wen, S., Du, X., Lu, T., Su, S. Y., Yang, X., et al. (2012). Toll-like receptor 3 ligand polyinosinic:polycytidylic acid promotes wound healing in human and murine skin. J Invest Dermatol 132, 2085-2092.

26. Liu, Y., Lyle, S., Yang, Z., and Cotsarelis, G. (2003). Keratin 15 Promoter Targets Putative Epithelial Stem Cells in the Hair Follicle Bulge. 121, 963-968.

27. Luis, NunoA M., Morey, L., DiÂ Croce, L., and Benitah, SalvadorÂ A. (2012a). Polycomb in Stem Cells: PRC1 Branches Out. Cell Stem Cell 11, 16-21.

28. Luis, N. M., Morey, L., Mejetta, S., Pascual, G., Janich, P., Kuebler, B., Cozutto, L., Roma, G., Nascimento, E., Frye, M., et al. (2012b). Regulation of human epidermal stem cell proliferation and senescence requires polycomb-dependent and -independent functions of Cbx4. Cell Stem Cell 9, 233-246.

29. Lundberg, A. M., Drexler, S. K., Monaco, C., Williams, L. M., Sacre, S. M., Feldmann, M., and Foxwell, B. M. (2007). Key differences in TLR3/poly I:C signaling and cytokine induction by human primary cells: a phenomenon absent from murine cell systems. Blood 110, 3245-3252.

30. Melkamu, T., Kita, H., and O'Grady, S. M. (2013). TLR3 activation evokes IL-6 secretion, autocrine regulation of Stat3 signaling and TLR2 expression in human bronchial epithelial cells. J Cell Commun Signal 7, 109-118.

31. Mescher, A. L. (1996). The cellular basis of limb regeneration in urodeles. The International journal of developmental biology 40, 785-795.

32. Millar, S. E. (2002). Molecular mechanisms regulating hair follicle development. J Invest Dermatol 118, 216-225.

33. Myung, P. S., Takeo, M., Ito, M., and Atit, R. P. (2013). Epithelial Wnt ligand secretion is required for adult hair follicle growth and regeneration. The Journal of investigative dermatology 133, 31-41.

34. Nelson, A. M., Loy, D. E., Lawson, J. A., Katseff, A. S., Fitzgerald, G. A., and Garza, L. A. (2013). Prostaglandin D(2) Inhibits Wound-Induced Hair Follicle Neogenesis through the Receptor, Gpr44. The Journal of investigative dermatology 133, 881-889.

35. Sanchez Alvarado, A. (2006). Planarian regeneration: its end is its beginning Cell 124, 241-245.

36. St-Jacques, B., Dassule, H. R., Karavanova, I., Botchkarev, V. A., Li, J., Danielian, P. S., McMahon, J. A., Lewis, P. M., Paus, R., and McMahon, A. P. (1998). Sonic hedgehog signaling is essential for hair development. Current biology: C B 8, 1058-1068.

37. Torok, M. A., Gardiner, D. M., Izpisua-Belmonte, J. C., and Bryant, S. V. (1999). Sonic hedgehog (shh) expression in developing and regenerating axolotl limbs. The Journal of experimental zoology 284, 197-206.

38. Uematsu, S., and Akira, S. (2007). Toll-like receptors and Type I interferons. J Biol Chem 282, 15319-15323.

39. Yan, C., Grimm, W. A., Garner, W. L., Qin, L., Travis, T., Tan, N., and Han, Y. P. (2010). Epithelial to mesenchymal transition in human skin wound healing is induced by tumor necrosis factor-alpha through bone morphogenic protein-2. The American journal of pathology 176, 2247-2258.

We claim:

1. A method for stimulating hair follicle neogenesis in a subject comprising the step of administering to the subject an effective amount of a TLR3 agonist.

2. The method of claim 1, wherein the TLR3 agonist is a double stranded RNA (dsRNA).

3. The method of claim 1, wherein the subject has alopecia.

4. The method of claim 1, wherein the subject is bald.

5. The method of claim 1, wherein the subject has a wound.

6. The method of claim 1, wherein the TLR3agonist is administered directly to a site on the subject that requires hair follicle neogenesis.

7. The method of claim 6, wherein the TLR3 agonist is administered topically.

8. The method of claim 7, wherein the TLR3 agonist is administered by injection.

9. The method of claim 1, wherein the TLR 3 agonist is Polyinosinic:polycytidylic acid (Poly I:C).

10. A method for treating common male pattern hair loss in a subject comprising the step of administering to the subject an effective amount of a TLR3 agonist.

11. The method of claim 10, wherein the TLR3 agonist is a double stranded RNA (dsRNA).

12. The method of claim 10, wherein the TLR3 agonist is administered directly to the site of hair loss on the subject.

13. The method of claim 12, wherein the TLR3 agonist is administered topically.

14. The method of claim 12, wherein the TLR3 agonist is administered by injection.

15. The method of claim 10, wherein the TLR3 agonist is Polyinosinic:polycytidylic acid (Poly I:C).

16. The method of claim 1, further comprising administering an effective amount of LL-37.

* * * * *

UNITED STATES PATENT AND TRADEMARK OFFICE
CERTIFICATE OF CORRECTION

PATENT NO. : 10,105,305 B2  
APPLICATION NO. : 15/120189  
DATED : October 23, 2018  
INVENTOR(S) : Luis Andres Garza and Amanda Marie Nelson Page 1 of 1

It is certified that error appears in the above-identified patent and that said Letters Patent is hereby corrected as shown below:

In the Claims

Please amend Claim 8 as follows:
8. The method of claim 6, wherein the TLR3 agonist is administered by injection.

Signed and Sealed this  
Second Day of July, 2019

Andrei Iancu  
*Director of the United States Patent and Trademark Office*